United States Patent
Sonobe et al.

(10) Patent No.: US 7,103,141 B2
(45) Date of Patent: Sep. 5, 2006

(54) SCAN TYPE DIGITAL X-RAY IMAGING APPARATUS

(75) Inventors: Kouichi Sonobe, Kyoto (JP); Takeshi Hayashi, Kyoto (JP); Makoto Honjyo, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 306 days.

(21) Appl. No.: 10/180,994

(22) Filed: Jun. 24, 2002

(65) Prior Publication Data

US 2003/0007602 A1 Jan. 9, 2003

(30) Foreign Application Priority Data

| Jun. 22, 2001 | (JP) | ............................. 2001-189031 |
| Dec. 19, 2001 | (JP) | ............................. 2001-386200 |
| Jun. 21, 2002 | (JP) | ............................. 2002-181548 |

(51) Int. Cl.
*A61B 6/14* (2006.01)
(52) U.S. Cl. .......................... 378/39; 378/108
(58) Field of Classification Search ............ 378/38–40, 378/96–97, 108–113, 98.7, 62, 156, 55, 98.8, 378/146, 195
See application file for complete search history.

(56) References Cited

U.S. PATENT DOCUMENTS

| 4,082,957 | A | * | 4/1978 | Morlan ........................ 378/156 |
| 4,641,336 | A | * | 2/1987 | Gastrin ........................ 378/156 |
| 5,058,147 | A | * | 10/1991 | Nishikawa et al. ........... 378/38 |
| 5,425,065 | A | * | 6/1995 | Jarvenin ....................... 378/40 |
| 5,454,023 | A | * | 9/1995 | Asikainen ................... 378/156 |
| 5,511,106 | A | * | 4/1996 | Doebert et al. ............. 378/146 |
| 5,793,838 | A | * | 8/1998 | Kovacs ......................... 378/39 |
| 5,828,720 | A | * | 10/1998 | Syrjanen ...................... 378/38 |
| 6,219,401 | B1 | * | 4/2001 | Tachibana et al. ............ 378/39 |
| 6,220,751 | B1 | * | 4/2001 | DiGiacomo et al. ........ 378/182 |
| 6,584,171 | B1 | * | 6/2003 | Suzuki et al. .............. 378/98.8 |

* cited by examiner

*Primary Examiner*—David V. Bruce
*Assistant Examiner*—Hoon Song
(74) *Attorney, Agent, or Firm*—Koda & Androlia

(57) ABSTRACT

A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from the X-ray generator for the object while the X-ray generator and the X-ray detector are synchronously moved in the same direction with the object interposed therebetween, thereby producing an X-ray image of the object. In the X-ray imaging apparatus, the scanning speed of the X-ray slit beam is controlled depending on the X-ray transmitted amount through the object to be examined detected by the X-ray detector during the X-ray beam scanning is performed, whereby soft and hard tissues appearing in the X-ray image are amended in each contrast and/or in each density.

28 Claims, 14 Drawing Sheets

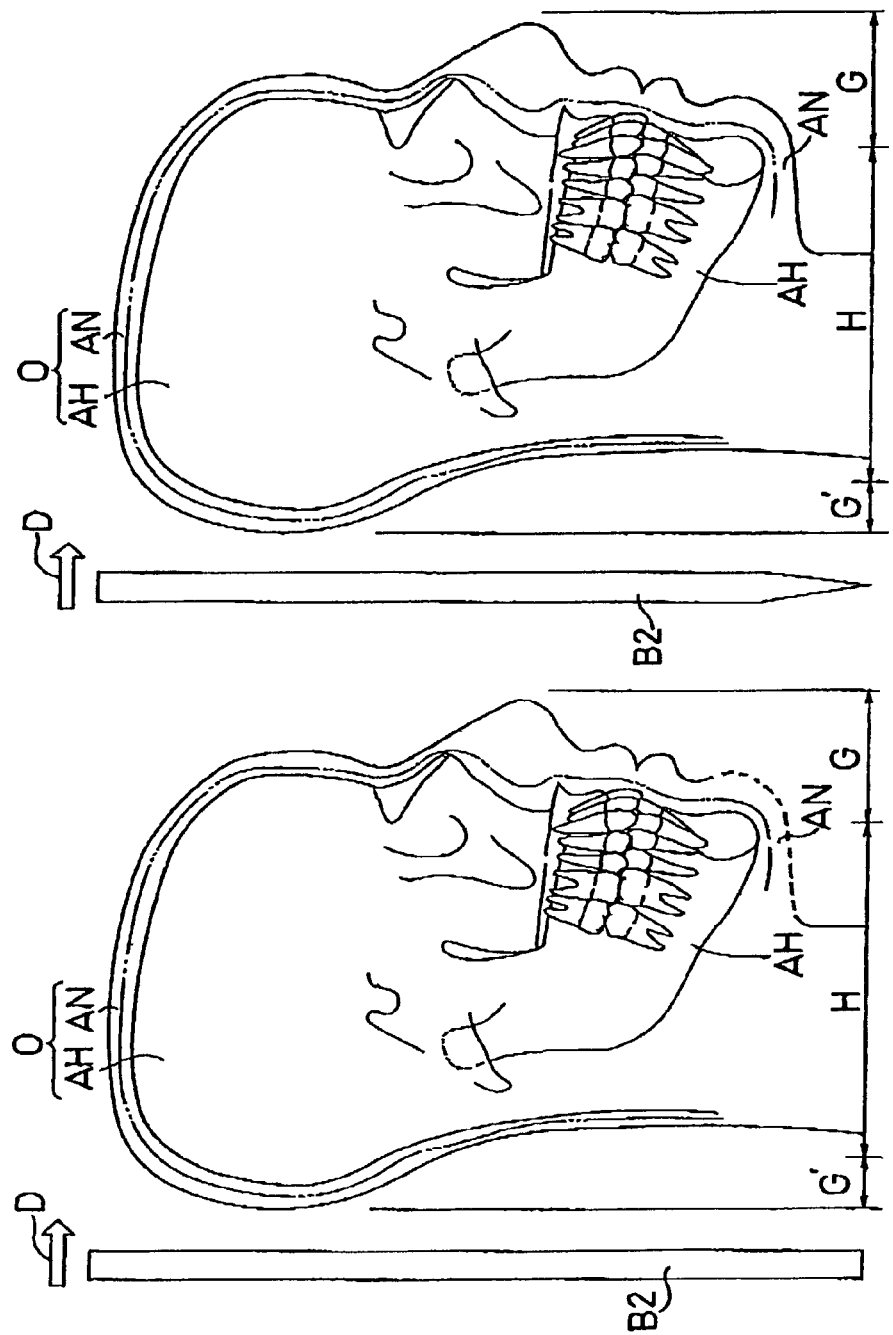

SCAN TYPE DIGITAL X-RAY IMAGING APPARATUS

BACKGROUND OF THE INVENTION

1. Field of the Invention

The present invention relates to an improvement of a scan type digital X-ray imaging apparatus which has an X-ray detector capable of outputting digitalizable data or digital data upon receiving X-ray like a dental digital cephalometric X-ray imaging apparatus and wherein the X-ray slit beam scans an object to be examined while the X-ray slit beam emitted from the X-ray generator and the X-ray detector are synchronously moved in the same direction and an X-ray image of the object is produced.

2. Prior Art

Conventionally, an X-ray slit beam has scanned the head of the patient, which is an object to be examined, to obtain an X-ray image by a scan type digital X-ray imaging apparatus for medical use for example a dental cephalometric imaging apparatus disclosed in JP-A-7-143981. However, according to such an apparatus, when trying to make an image of a hard tissue such as a skull and a dental jaw bone clear by emitting a X-ray slit beam uniformly onto the head to be scanned, the images of a soft tissue such as skin and lips haven't been made clear. In contrast, the images of a hard tissue haven't been obtained when trying to make images of soft tissues clear by doing the same as mentioned above.

JP-A-7-8483 discloses an apparatus for solving the above-mentioned problems.

Namely the apparatus has a soft tissue filter, in which before an X-ray slit beam is radiated on the patient's head, a soft tissue filter which has a similar shape to a soft tissue area of a head is provided for a passage of the X-ray beam, thereby obtaining the image of the soft tissue. However, it has been difficult to adjust the position of the soft tissue filter on an actual soft tissue area of the patient's head so that accurate separation of the soft tissue area has been unable, further it has been required to prepare plural soft tissue filters depending on the size of the patient's head.

JP-A-5-252444 and JP-A-9-266901 propose a method wherein the data obtained by an X-ray detector is image processed to distinguish a hard tissue area and a soft tissue area and a gradation process is executed depending on the hardness of the tissue. However, such image processing has been complicated.

For example, according to the dental X-ray panoramic imaging apparatus as described in JP-A-8-19534, when an X-ray slit beam is radiated while rotating an X-ray generator and an X-ray detector opposing each other around the object, the rotational speed is controlled depending on the number of hard tissues existing on the passage of a beam, thereby obtaining the image of the hard tissue area even if plural bones are overlapped. However, in such a case, there has been no consideration on soft tissues and an X-ray slit beam have been rotatably radiated around the object unlike the dental digital cephalometric X-ray imaging apparatus wherein an X-ray slit beam scans the object.

SUMMARY OF THE INVENTION

The object of the present invention in order to solve the above-mentioned problems is to provide a scan type digital X-ray imaging apparatus wherein the dynamic range of an X-ray image is enlarged by a simple operation despite of being scan type apparatus, whereby improved digital X-ray images which is clear both in its hard tissue area and a soft tissue area are obtained.

The other objects and merits of the present invention will be clarified when further reading this specification.

The applicant of the present invention proposes a scan type digital X-ray imaging apparatus having several kinds of characteristics, for example, the apparatus wherein the scanning speed and/or the output intensity of an X-ray are controlled while an X-ray slit beam is scanned, a gradation process is executed after X-ray beam scanning, and a position detection means is provided for detecting a reference point required for its density and/or its contrast correction are proposed.

According to the present invention, the correction in density and/or the correction of contrast in both of the hard tissue region and the soft tissue region are added, whereby both of them are made clear.

It is well known that the following relation exists between X-ray density and X-ray intensity.

An X-ray density D is calculated from the next function.

Here, $D=f(It^p)$, wherein I=X-ray intensity, t=exposure time.

Also, X-ray intensity is calculated from the next function.

Here, $I=kV^2it$, wherein V=tube voltage, i=tube current, t=exposure time.

From the above, it should be understood that X-ray density can be controlled by varying X-ray intensity, and/or exposure time, while X-ray intensity can be controlled by varying tube voltage, tube current and/or exposure time and therefore in the present invention, these element are directly or indirectly controlled for correcting an X-ray density and/or X-ray intensity, thereby making X-ray image clear both in its hard tissue region and its soft tissue region.

The scan type digital X-ray imaging apparatus proposed here according to the present invention has basic construction as follows.

Namely the present apparatus comprises an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray generator for said object while said X-ray generator and said X-ray detector are synchronously moved in the same direction with said object interposed therebetween, thereby producing an X-ray image of the object.

The proposed scan type digital X-ray imaging apparatus is explained according to each embodiment as below.

According to the first embodiment of the proposed apparatus, the scanning speed or the output intensity of the X-ray slit beam or both are controlled depending on the X-ray transmitted amount detected by the X-ray detector during X-ray scanning for producing improved X-ray image.

The control factors of the scanning speed, or the output intensity or both are feedback controlled such that the X-ray transmitted amount during X-ray scanning accords with a control target data prepared in advance according to an object to be examined.

FIG. 14 shows relation between an X-ray slit beam and the head of an object to be examined according to the present invention.

In the present invention, a scanning speed of X-ray slit beam is controlled according to a region of an object to be examined by changing a pulse rate preset in a pulse motor for scan driving under a condition that both of a tube current and a tube voltage maintain constant, for example at 4 mA for tube current, at 80 Kv for tube voltage as in a manner described below so that the scanning speed of X-ray is controlled at such speed curve shown at Y in FIG. 14.

Various pulse rates to be employed in the apparatus are prepared for various kinds of object to be examined such as adults, children, and women and further imaging directions and stored in a memory provided in the apparatus, however in case that such pulse rate cannot be applied, other pulse pattern may be further employed.

Therefore, according to such an X-ray imaging apparatus, the whole of X-ray image is corrected so as to enlarge its dynamic range while scanning with X-ray slit beam in a manner that the scanning speed of an X-ray is increased by adding correction to the reference pulse rate when the X-ray transmitted amount detected by the detector increases, while the scanning speed of X-ray is decreased by adding correction to the reference pulse rate when the X-ray transmitted amount detected by the X-ray detected decreases.

The X-ray tube current and/or X-ray tube voltage may be further controlled in addition to the controlling of scan speed of X-ray slit beam above mentioned when the controlling of X-ray scanning speed is insufficient.

In this case, the intensity of X-ray slit beam is controlled by changing a tube current, a tube voltage or both, thereby enlarging the dynamic range of the X-ray image in both of the hard and the soft tissue region.

Here in such region that X-ray transmitted amount is large, X-ray slit beam scans a soft tissue area of an object, in such occasion the irradiation dosage of X-ray slit beam emitted on the soft tissue area per a unit time is reduced by increasing the scanning speed of X-ray, wile the X-ray detector receives X-ray moving synchronism with X-ray slit beam at a synchronous speed.

As a result, the dynamic range of X-ray image in the soft tissue area is improved.

On the other hand, in such region that X-ray transmitted amount is small, X-ray slit beam scans a hard tissue area of an object, in such occasion the irradiation dosage of X-ray slit beam emitted on the soft tissue area per a unit time is increased by reducing the scanning speed of X-ray, while the X-ray detector receives X-ray moving synchronism with X-ray slit beam at a synchronous speed.

As a result, the dynamic range of X-ray image in the hard tissue area is also improved.

FIG. 14a and FIG. 14b are graphic data showing the principle of the present invention, wherein the control method according to the present invention which is carried out with a tube current and a tube voltage constant is depicted for easy understanding, comparing to the reference control method in which X-ray beam slit is scanned at constant speed.

Xo shows an X-ray transmitted amount per second, detected by the X-ray detector under a condition that X-ray slit beam scans the head of an object at constant speed, which is applied in order for the soft tissue region of an object to appear clear in this reference control.

Accordingly when Xo is applied, the X-ray image of which the soft tissue region is clear in its density can be obtained because the X-ray detector detects the transmitted amount in appropriate sensitivity range of the X-ray detector depending on the difference of X-ray absorption coefficient in its region of an object, however while the hard tissue region in X-ray image does not appear, i.e. all the corresponding part in the X-ray image become white in appearance because X-ray transmitted amount is markedly decreased in their region, thereby the X-ray transmitted amount detected by the X-ray detector drops down below the minimum sensitivity level Xmin.

Contrast to that, the X-ray transmitted amount is applied, which is not shown here, in order for the hard tissue region in X-ray to be clear, the X-ray image in the hard tissue region is clear in its density because the X-ray detector detects the transmitted amount in appropriate sensitivity range of the X-ray detector depending on the difference of X-ray absorption coefficient in its region of the object, while the soft tissue region in X-ray image does not appear, i.e. all the corresponding part in X-ray image become black in appearance because X-ray transmitted amount is markedly increased in their region, thereby the X-ray transmitted amount detected by X-ray detector raises above the maximum sensitivity level Xmax and thereby the output from the detector become saturated.

In view of the above, in the present invention, the scanning speed of X-ray slit beam is controlled so as to exist the X-ray transmitted amount in both region of the soft tissue and the hard tissue detected by the X-ray detector exist between the minimum level Xmin of the sensitivity and the maximum level Xmax of the sensitivity of the X-ray detector.

FIG. 14b shows change Y in X-ray slit beam scanning speed when the present invention is carried out under such condition, corresponding to FIG. 14a.

It is understood from the FIG. 14b that X-ray scanning speed becomes fast in the soft tissue region but slow in the hard tissue region, thereby X-ray transmitted amount is controlled under such condition above mentioned, so that X-ray image appropriate in density and/or in its contrast can be obtained.

And also it is understood that X-ray transmitted amount Xo prior to the controlling according to the present invention is made flat as shown at X, after the controlling which is applied to the present invention.

The base principle of the present invention exists in that the X-ray amount is controlled for the hard and the soft tissue region in an object to be examined so as to correct their density and their contrast under a condition that the X-ray transmitted is maintained between the minimum level Xmin of the sensitivity and the maximum level Xmax of the sensitivity of the X-ray detector while X-ray scanning for said object is performed.

And gradation process may be further executed after X-ray scanning for producing clearer X-ray image.

According to the present invention, the dynamic range for both the soft tissue region and the hard tissue region in one X-ray image can be improved and enlarged, thereby obtaining the X-ray image clear in both the soft tissue region and the hard tissue region of the object.

In case that the scanning speed of X-ray slit beam is controlled, various type of controlling may be applied in the present invention, one of which is realized by adding correction to the pulse rate of pulse motor for scan driving, various controlling being prepared and stored in a memory provided in the apparatus.

Accordingly, the base principal of the present invention exists in that X-ray transmitted amount detected by the X-ray detector scanning an object to be examined is held both for the soft tissue region and for the hard tissue region between the maximum level Xmax and the minimum level Xmin while X-ray scanning is performed, however in case that more clear X-ray image is desired for examination, gradation process as mentioned later may be further given to the image produced by the X-ray scanning as mentioned above, in such case appropriate reference point for gradation prepared in advance is also employed.

According to the present invention, the dynamic range both in the soft tissue and the hard tissue is enlarged by the principle mentioned above and an X-ray images in which the soft tissue region and hard tissue region in one image are clearly comprehended can be produced.

For controlling the output intensity of the X-ray slit beam, each one of a tube current in the X-ray tube for generating the X-ray slit beam and its tube voltage, or both of them may be controlled.

In the modification of the first embodiment, a simulation model is defined in advance wherein an X-ray transmitted amount is expected corresponding to the object fixed with the object fixing means and the simulation model is used for contrast correction. Thus the control factors such as scanning speed of the X-ray slit beams and so on as mentioned above are controlled.

The expected X-ray transmitted amount is not the X-ray transmitted amount obtained by emitting an X-ray beam on the object but the simulation model for the X-ray transmitted amount prepared for the object in advance, therefore, a time delay for obtaining an actual value isn't caused and high control response can be obtained.

Further, in the modification of the first embodiment, a position detection means is provided for detecting a gradation process reference point of the object. The control factors such as the scanning speed of the X-ray slit beams are controlled depending on the output of the position detection means.

According to such modification, X-ray density correction and/or more accurate contrast correction can be executed because the correct gradation process reference point, namely the reference point showing where the X-ray absorption coefficient changes, is detected at X-ray photography.

According to the second embodiment of the present invention, the X-ray image obtained by scanning with the X-ray slit beams is gradation processed depending on the scanning speed and the output intensity of the X-ray slit beam having scanned the object.

In such an embodiment, the dynamic range isn't improved by controlling the irradiation amount (scanning speed or output intensity) of the X-ray slit beam per time unit when an X-ray image is produced in order to obtain clear images of both soft tissue area and the hard tissue area. However, in the embodiment, a gradation process is executed for the soft tissue area depending on the scanning speed and/or the output intensity of the X-ray slit beams for the X-ray image obtained by scanning with the X-ray beam, therefore, the density is corrected and/or contrast of the X-ray image is emphasized more accurately so that the dynamic range of the X-ray image is improved.

The area for emitting the X-ray slit beam for improving the dynamic range of the X-ray image by controlling the scanning speed and the output intensity is the region where the X-ray absorption coefficient is different, namely the gradation of the X-ray image is different. Therefore, analyzing the scanning speed or the output intensity, it can be distinguished which part is to be gradation processed. Utilizing it, the gradation process is executed for the resulting X-ray image and an X-ray image in which both soft tissue area and the hard tissue area are more clearly understood can be obtained.

The gradation process for the X-ray image obtained by scanning the object with the X-ray slit beam can be controlled depending on an expected X-ray transmitted amount during scanning and such a scan type digital X-ray imaging apparatus is proposed herein.

In this case, when the gradation process is executed depending on the actually measured X-ray transmitted amount, better gradation process is possible at real time. On the other hand, when the gradation process is executed depending on an expected X-ray transmitted amount, more simple gradation process is possible.

Further, in the third embodiment proposed in the present invention, a position detection means is provided for detecting a gradation process reference point position of the object. Depending on the output of the position detection means, a filter gradation process is executed for the X-ray image obtained by the X-ray detector for emphasizing the contrast of the X-ray image.

The filter gradation process means a process wherein positioning is executed at the gradation process reference position, a filter pattern such as a soft tissue area prepared in advance is applied to the obtained X-ray image and the density of the X-ray image is controlled only on the filter pattern area.

According to the X-ray imaging apparatus, the gradation process is executed after imaging is finished, therefore, the X-ray irradiation amount control before starting imaging isn't required. So, only a simple addition is required without image processing the entire X-ray image, thereby achieving usability.

Further, as the filter pattern of the soft tissue area is only required to be prepared as digital data, several actual soft tissue area filters need not to be prepared as a hardware.

According to this embodiment, when the X-ray image obtained by the X-ray detector is filter gradation processed, the gradation process depending on the scanning speed and/or output intensity of the X-ray slit beam having scanned the object, after scanning with the X-ray slit beam, is also included.

In such an X-ray imaging apparatus the gradation process depending on the X-ray irradiation data is added on the filter gradation process, therefore both effects can be multiply achieved.

For executing the gradation process of the X-ray image which is under photography or after photography depending on the object, a scan type digital X-ray imaging apparatus having a position detection means for detecting the gradation reference point of the object is further proposed. Such an apparatus includes a position detection means having a contacting detector to be used while contacting with the object or a non-contacting detector to be used without touching the object.

Further in a preferable embodiment of the present invention, the imaging apparatus is constructed such that the X-ray slit beam and the X-ray detector are synchronously moved with an X-ray tube provided on the X-ray generator fixed thereon, by moving a primary slit provided adjacent to the X-ray tube and a secondary slit provided on the X-ray generator side of the object fixing means, together with the X-ray detector in the same direction. In such an embodiment, the X-ray tube provided for the X-ray generator is fixed without moved or rotated, instead, the primary slit for restricting the X-ray beam generated from the X-ray tube at a fixed area at its emitting part can be synchronously moved with the secondary slit further defining the X-ray beam before emitting on the object.

Accordingly, the X-ray tube, being the center of irradiation, is fixed so that X-ray beam scanning can be executed without run-out of its center and more clear X-ray image can be obtained.

Still further in a preferable embodiment of the present invention, an X-ray detector comprised of a semiconductor detector such as a CCD camera is provided and the X-ray slit beam and the X-ray detector are synchronously moved relative to the object in an up and down direction normal to the irradiation direction of the X-ray slit beam or in a right or left direction to the irradiation direction of the X-ray slit beam.

In more concrete embodiments of such an X-ray imaging apparatus, a dental digital cephalometric X-ray imaging apparatus is explained wherein the object fixing means is comprised of a head fixing means, however, the present invention isn't limited to such an apparatus.

The fourth embodiment proposed here is characterized in that the X-ray irradiation amount to an object is controlled when X-ray slit beam is scanned like as the first embodiment mentioned above, and the irradiation energy of X-ray is not controlled in a synchronous movement direction but the apparatus is provided with a vertical filter for changing irradiation energy of X-ray along a direction normal to said synchronous movement direction, whereby the dynamic range of X-ray image can be also enlarged with respect to such object that the hard tissue region and the soft tissue region are arranged along a direction normal to said synchronous movement direction.

And in case that the filter is constructed as such one as to be detachable, the filter is removed when unnecessary and attached to when demanded depending on an object and such filter may be attached to the X-ray detector or the X-ray generator or both.

BRIEF DESCRIPTION OF THE DRAWINGS

FIG. 5 shows application of the position detection means shown in FIG. 2, wherein FIG. 5a is seen from right side.

FIG. 8 shows an external view of the scan type digital X-ray imaging apparatus shown in FIG. 1, wherein

FIG. 9 is a detailed view of the X-ray detector shown in FIG. 1, wherein

FIG. 12a is an explanatory view of an X-ray image obtained without using the vertical filter and FIG. 12b is an explanatory view of an X-ray image obtained using the vertical filter. FIG. 12a is a fragmentary view in a direction of arrow V3 in FIG. 11b.

FIG. 13a1, FIG. 13b1, FIG. 13c1, FIG. 13d1 and FIG. 13e1 are front views, and FIG. 13a2, FIG. 13e2, FIG. 13f2, FIG. 13g2 and FIG. 13h2 are its side views respectively.

DETAILED DESCRIPTION OF THE INVENTION

Embodiments of the present invention will be explained with reference to the attached drawings.

Referring to the FIGS. 1–14, embodiments wherein a scan type digital X-ray imaging apparatus for medical use of the present invention is applied to a dental cephalometric imaging apparatus will be explained hereinafter, however, the present invention is not limited to dental use alone but is widely applied to an X-ray imaging apparatus for general medical use, such as a mammography, and slit radiography, and so on.

Figure 1:
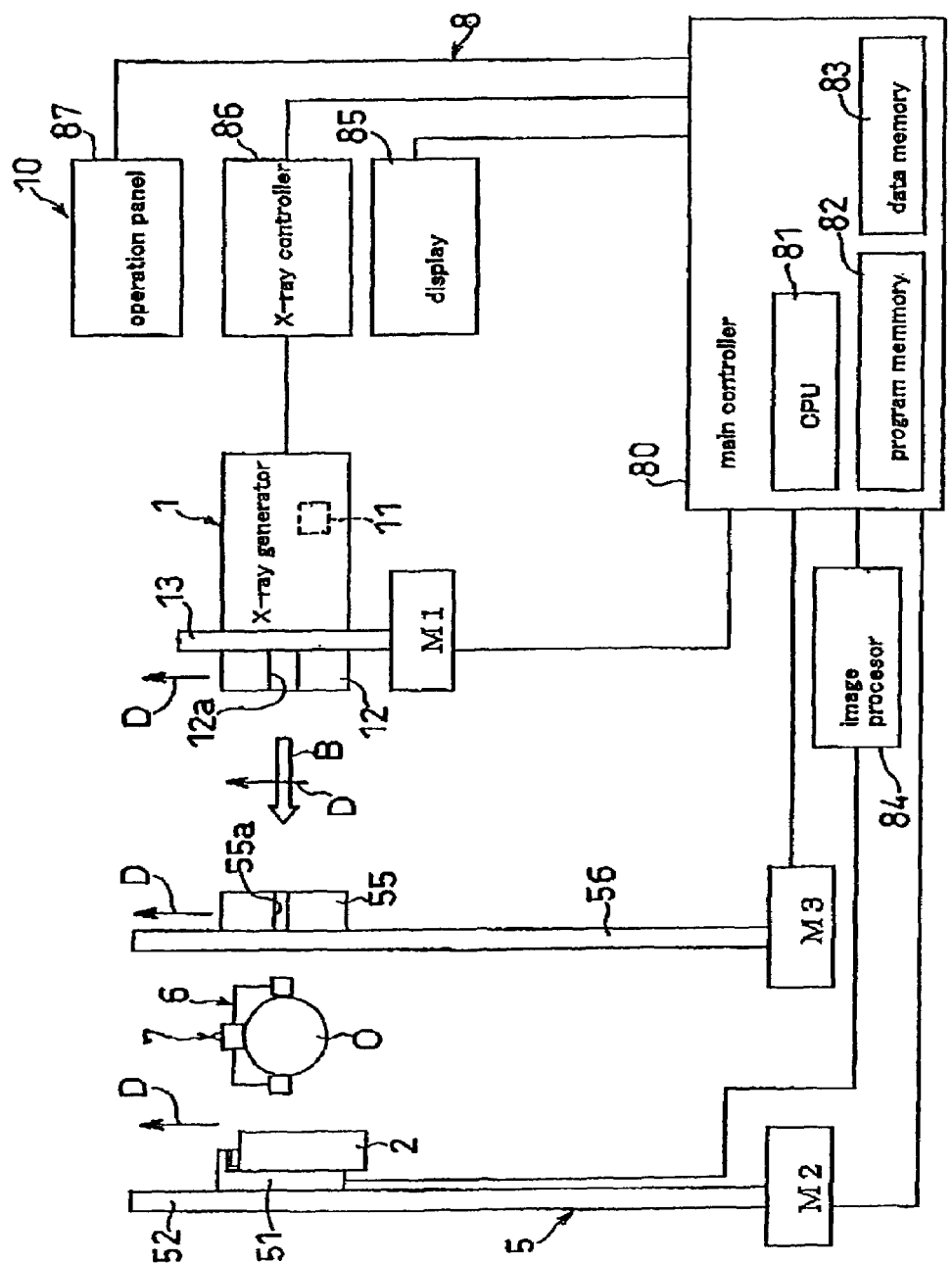
FIG. 1 is a block diagram showing an entire construction of one embodiment of a scan type digital X-ray imaging apparatus for medical use according to the present invention.

FIG. 1 is a block diagram showing an entire construction of one embodiment of a scan type digital X-ray imaging apparatus for medical use according to the present invention.

The scan type digital X-ray imaging apparatus for medial use 10 has an X-ray generator 1, an X-ray detector 2 for receiving X-ray slit beams B emitted from the X-ray generator 1 and transmitted through an object O and for outputting the received X-ray data in the form of digital or digitalizable data, a support for scanning detector 5 for transferring and holding the X-ray generator 2 so as to be detachable and able to control its speed, an object fixing means 6 for fixing an object O, a position detection means 7 for detecting the position of a gradation process standard point of the object, and a controller 8 for controlling the entire apparatus.

FIG. 1 shows a plan view of the X-ray generator 1, the X-ray detector 2, the support for scanning detector 5, the object fixing means 6, and the position detection means 7 when their using condition is seen from above.

The X-ray generator 1 includes an X-ray tube 11 and a primary slit member 12 made of an X-ray shielding material. The slit member 12 has a primary slit 12a which is an opening for restricting the X-ray beams generated widely from the X-ray tube 11 in a predetermined direction and in a predetermined area in order to radiate only on an objective area. The X-ray generator 1 also has a primary slit moving axis 13 for moving the primary slit member 12 in a direction of D as shown in the figure so as to be able to control the speed and position and has a primary slit moving motor M1 such as a pulse motor for driving the moving axis 13.

The X-ray generator 2 will be detailed with reference to FIG. 5 later.

The support for scanning detector 5 is provided with a detector holder 51 for detachably holding the X-ray generator 2, a detector moving axis 52 for moving the detector holder 51 in direction D as shown in the figure so as to be able to control the speed and position, a detector moving motor 2 such as a pulse motor for driving the moving axis 52, a secondary slit member 55 made of an X-ray shielding material and having a secondary slit 55a which is an opening for restricting the X-ray beams passing therethrough further in a predetermined area before the X-ray slit beams B restricted by the primary slit 12a of the X-ray generator 1 are radiated on the object, a secondary slit moving axis 56 for moving the secondary slit member 55 in direction D as shown in the figure so as to be able to control the speed and position, and a secondary slit moving motor M3 such as a pulse motor for driving the moving axis 56.

The detector moving motor M2 and the secondary slit moving motor M3 may be mechanically linked by means of a timing belt without providing them separately and in such a case one of the motors is not necessarily provided.

The object fixing means 6 is constructed so as to fix the object in a predetermined position irrespective of the movement of the detection holder 51 of the support for scanning detector 5 and the movement of the secondary slit member 55 in direction D.

The position detection means 7 is fixedly supported to the object fixing means 6 and its detail is explained hereinafter with reference to FIG. 2, FIG. 5 and FIG. 6.

The controller 8 is comprised of a microcomputer and is provided with a main control part 80 having a central processing unit 81 for achieving a central control function of the controller 8, a program memory 82 for storing several kinds of control programs for processing in the central processing unit 81, and a data memory 83 for storing the obtained X-ray image data and control data. The controller 8 is further provided with an image processing unit 84 for image processing the X-ray receiving data obtained via the detector holder 51 from the X-ray detector 2 and outputting to the main control part 80, a display unit 85 for showing the X-ray images obtained in the main control part 80, an X-ray control unit 86 for controlling the tube current and tube voltage in the X-ray tube 11 of the X-ray generator 1 by means of an order from the main control part 80, and an operation panel 87 for receiving several operational instructions for the entire apparatus and outputting into the main control part 80.

The main control part 80 of the controller 8 is connected with the primary slit moving motor M1, the detector moving motor M2, and the secondary slit moving motor M3 so that the motors M1, M2 and M3 are controlled by the main control part 80.

According to the X-ray imaging apparatus 10, as shown in the figure, the X-ray generator 1 and the X-ray detector 2 are provided so as to interpose the object fixing means 6. It is characterized in that the X-ray generator 1 is kept fixed in relation to the object O held by the object fixing means 6, the object O is scanned by the X-ray slit beams B while synchronously moving the X-ray slit beams B radiated from the X-ray generator 1 and the X-ray detector 2 in the same direction D by moving the primary slit 12a and the secondary slit 55a synchronously. Thereby, the X-ray image of the object O can be obtained in the form of digital data. It is further characterized in that the scanning speed of the X-ray slit beams B (moving speed into direction D) is controlled depending on the X-ray transmitted amount which is the scanning X-ray receiving data obtained by the X-ray detector 2.

If the X-ray transmitted amount is large, the scanning speed of the X-ray slit beams B is controlled to be increased and if the transmitted amount is small, it is controlled to be reduced.

The former case is where a soft tissue area is scanned, wherein the dose of X-ray slit beams B radiated on the soft tissue area per unit time is reduced by increasing the scanning speed, and as a result the dose of the X-rays transmitted through the soft tissue area reduces because the X-ray generator 2 receives X-rays while moving synchronously.

On the other hand, the case where the transmitted amount is small is where a hard tissue area is scanned. In such a case the dose of the X-ray slit beams B radiated on the hard tissue area per unit time increases by reducing the scanning speed. As a result, the dose of the X-rays transmitted through the hard tissue area increases because the X-ray detector 2 receives X-rays while moving synchronously.

Thus, the dynamic range improves and the X-ray transmitted dose, namely the image density, is more uniformed as a whole, thereby obtaining the X-ray images in which the soft tissue area and the hard tissue area can be clearly comprehended.

The irradiation amount of the X-ray slit beams B on the object is increased or reduced by controlling the scanning speed of the X-ray slit beams B as mentioned above. Further, it can be carried out by controlling the irradiation output while keeping the scanning speed constant, thereby achieving the same results.

Specifically in this case, one of the tube current and the tube voltage in the X-ray tube 11 of the X-ray generator 1 may be controlled or both of them may be controlled by an X-ray controller 86. If both of them are controlled, its dynamic range becomes wider and the density of the soft tissue area and the hard tissue area becomes uniform in a wide area. In other words, each image can be clear.

Further, the above-mentioned control of the scanning speed and the irradiation output can be exercised together in order to control the irradiation amount of X-ray slit beams B on the object. Accordingly, its dynamic range becomes further wider and the density of the soft tissue area and the hard tissue area becomes uniform in a wide area. In other words, each image can be clear.

An expected X-ray transmitted dose prepared in advance may be used, not the X-ray transmitted dose actually received by the X-ray detector 2 as mentioned above, to control the irradiation amount of X-ray slit beams B. In such a case, time delay for waiting a measured value is not caused, thereby improving follow-up of control.

Specifically, because it is understood that the soft tissue is limited on the skin surface and the hard tissue exists in the center of the head part including large bone tissues, an imaging start point and finish point which are close to the skin surface are determined as a soft tissue and between those points are determined as a hard tissue. General control patterns depending on such an idea are stored in advance to control according to the data. In this case a selection switch may be used for distinguishing an adult or a child depending on the object's size.

Further, the same embodiment as the above-mentioned case wherein an actual value of the X-ray transmitted dose is used is possible, thereby achieving the same effect.

The direction D is not limited to the direction shown in the figure and may be opposite or a vertical direction in the figure (direction D' in FIG. 8).

Figure 2:
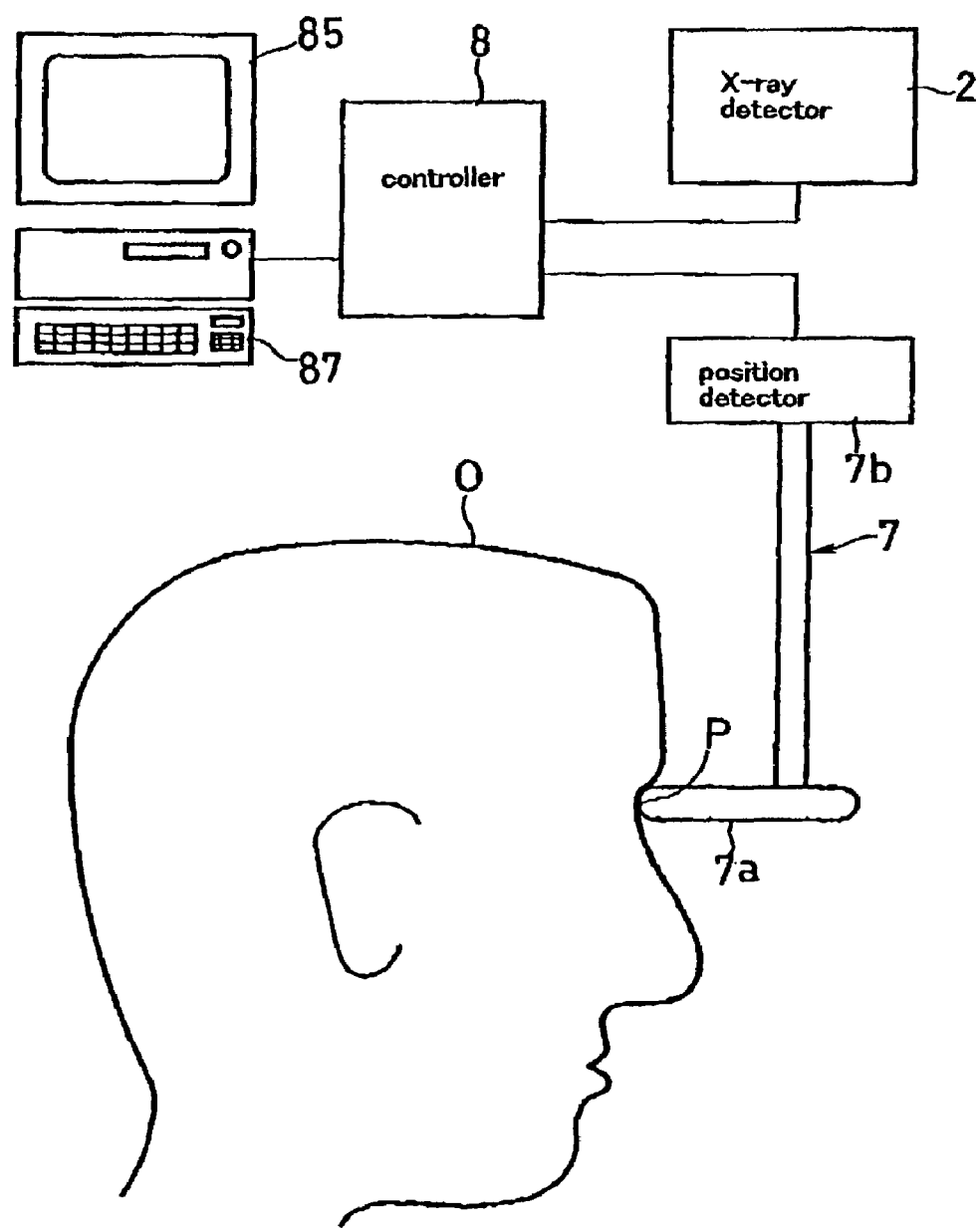
FIG. 2 is an explanatory view of the essential part of the position detection means shown in FIG. 1.

FIG. 2 is an explanatory view of the essential part of the position detection means in FIG. 1 and the same members which have been already explained are not detailed hereinafter. Like parts are shown by corresponding reference characters.

The position detection means 7 is provided with a contacting detector 7*a* and a position detector 7*b*. The position detector 7*b* supports the contacting detector 7*a* so as to be adjustable in up and down or back and forth direction as shown by the arrows in the figure and to be able to detect the position of a gradation process standard point P by detecting the position of the contacting detector 7*a* when the contacting detector 7*a* touches the standard point P of an object O (human head in this embodiment). The position detector 7*b* is fixed to the object fixing means 6 and is comprised of a potentiometer.

According to such a position detection means 7, the position of the gradation process standard point P (in this example, nasion often used in a digital cephalometric radiography in this embodiment, namely a forefront of nasoforehead suture in a median plane of a human head which is required for orthodentic therapy) can be detected easily and accurately in a short time. Further, it is not required to put an unnecessary mark on a patient's head.

The gradation process standard point P is not limited to the position of the nasion and any well-known positions can be used.

Thus obtained gradation process standard point position is used for executing expost gradation processing in a soft tissue area for the X-ray images obtained by the X-ray detector 2 or for controlling the irradiation amount of X-ray slit beams B during X-ray imaging.

Figure 3:
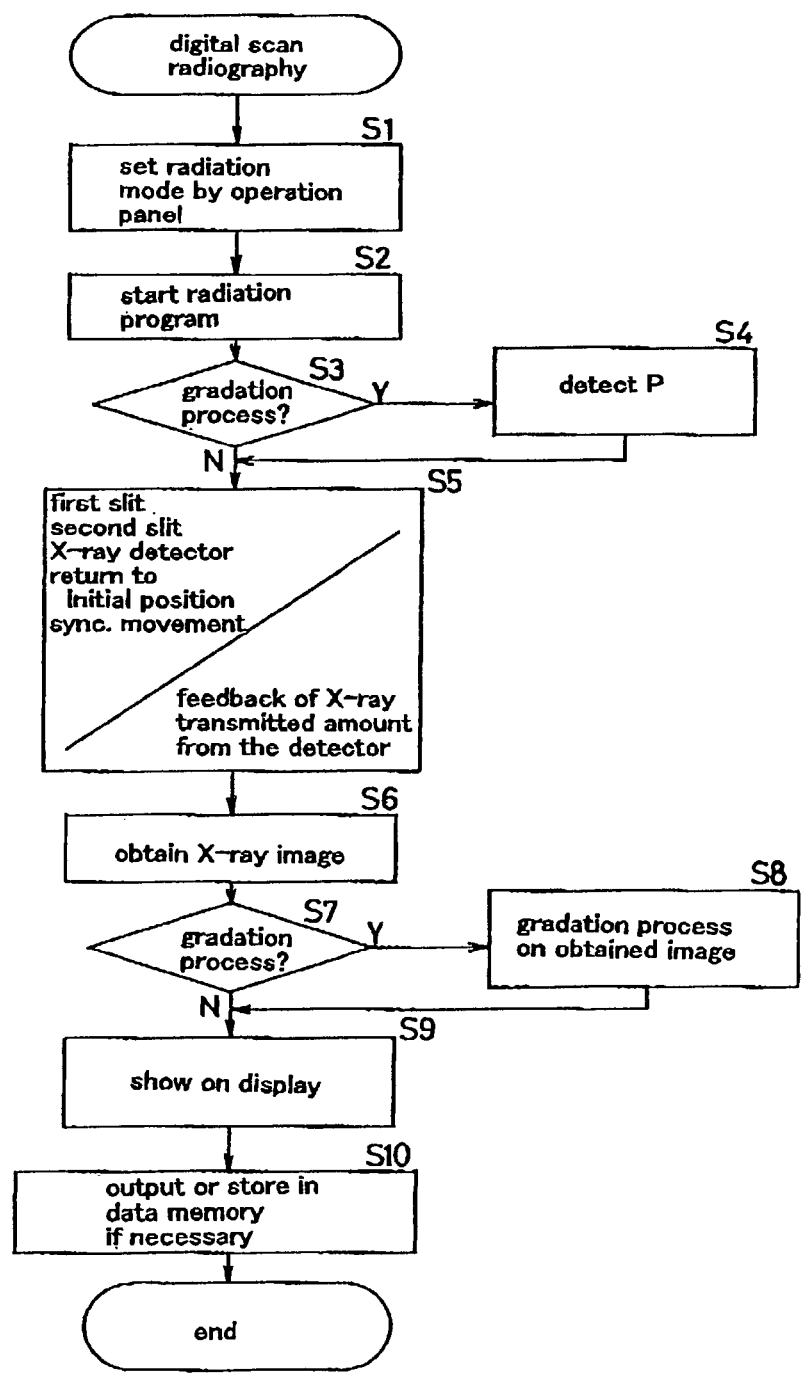
FIG. 3 is a flow chart showing digital scan imaging procedures according to the scan type digital X-ray imaging apparatus shown in FIG. 1.

FIG. 3 is a flow chart showing digital scan imaging procedures according to the medical scan type digital X-ray imaging apparatus in FIG. 1.

Any one of projection mode, namely imaging by controlling a scanning speed, imaging by controlling a irradiation output (tube voltage and/or tube current in the X-ray tube 11), imaging by gradation process such as a soft tissue area, as mentioned above, and a combination thereof may be selected by the operation panel 87 (S1).

When a projection program is started (S2), the gradation process standard point position is detected by the position detection means 7 as explained in FIG. 2 in case gradation process is selected (S3, S4).

Then the primary slit 12*a*, the secondary slit 55*a* and the X-ray detector 2 are returned to their initial positions and start to move synchronously in the same direction D as shown in FIG. 1. X-ray projection, that is scanning of X-ray slit beams B, is executed and the light receiving X-ray data obtained by the X-ray detector 2, namely X-ray transmitted amount, is fed back into the main control part 80 during scanning. Accordingly, depending on the selected projection mode, the irradiation amount of X-ray slit beams B is controlled by controlling the speed of the synchronous moving of the primary slit 12*a* and the secondary slit 55*a* which is a scanning speed of the X-ray slit beams B, and controlling the irradiation output of the X-ray slit beams B (tube voltage and/or tube current in the X-ray tube 11)(S5).

It is possible to use an expected X-ray transmitted amount prepared in advance depending on an object body instead of the X-ray transmitted amount obtained in the X-ray detector 2 as mentioned above. Further, it is possible to control the irradiation amount of X-ray slit beams B as the basis for the detected gradation process standard point position. In such a case, control is executed depending on the standard point showing the position where the X-ray absorption coefficient of an object changes, thereby accomplishing more accurate control.

Once the X-ray images are thus obtained (S6), gradation process is further executed for the obtained X-ray images when gradation process is selected (S7, S8) and the X-ray images, not processed, are displayed on the display unit 85 while gradation process is not selected (S9).

Such a gradation process may be executed on the basis of the control amount of X-ray irradiation amount (like scanning speed and irradiation output of the X-ray slit beams) when the X-ray images are obtained (in this case the gradation process standard point position is not always necessary). Or filter gradation process may be executed wherein positioning is executed at the gradation process standard point position, filters such as a soft tissue area prepared in advance are applied to the obtained X-ray images and the concentration of the X-ray images only in the filtered area is adjusted.

The X-ray images shown on the display unit are printed out or stored in a data memory 83 as the need arises (S10).

Figure 4:
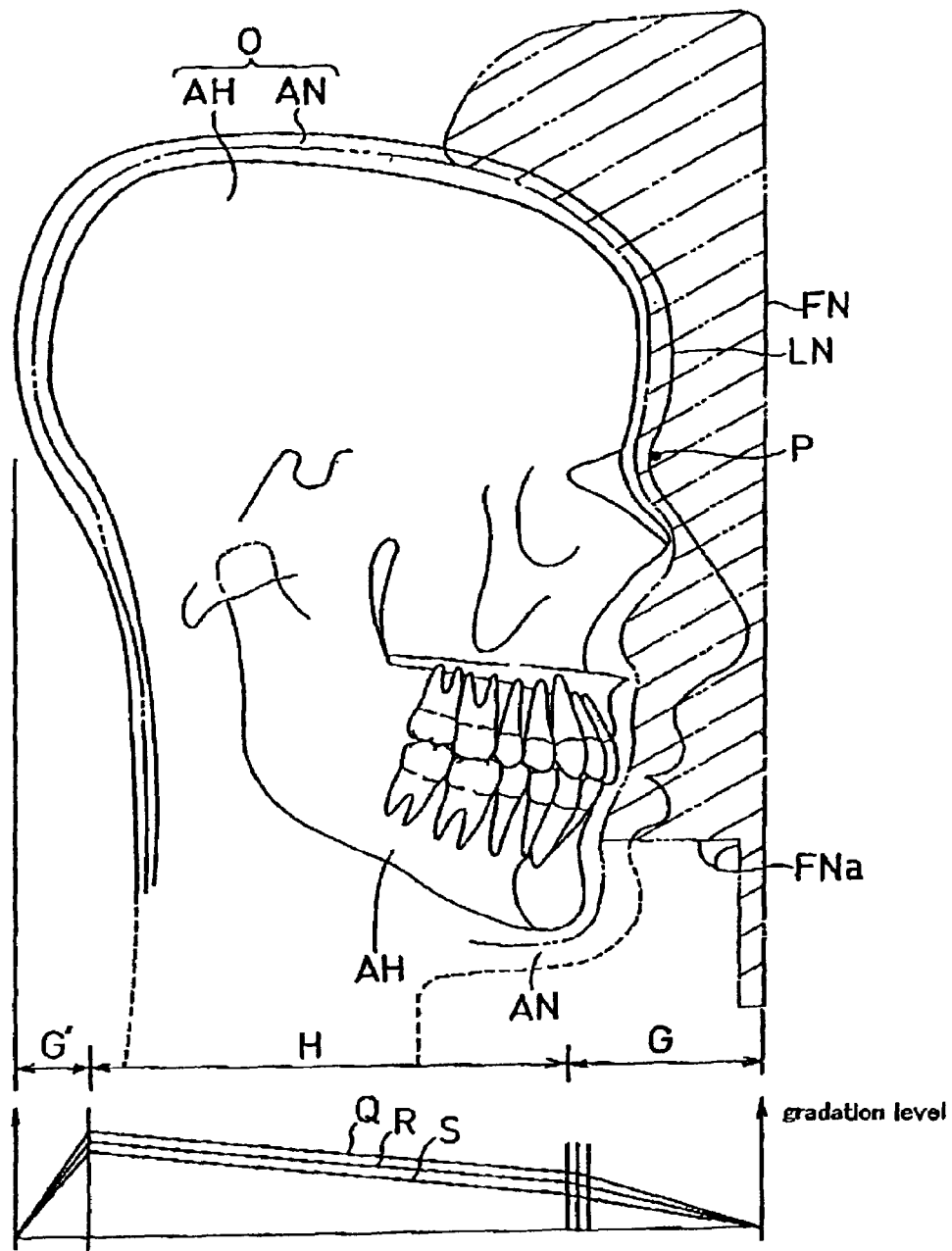
FIG. 4 shows one example of the X-ray images obtained by the scan type digital X-ray imaging apparatus in shown FIG. 1.

FIG. 4 shows one example of the X-ray images obtained as mentioned above by the scan type digital X-ray imaging apparatus in FIG. 1.

The X-ray image in the figure is a conceptual image which is obtained by projection under controlling the scanning speed and by projection under controlling the irradiation output and by executing gradation process. The reference character AH in the figure is a hard tissue area (skull or jaw bone in this embodiment), AN is a soft tissue area (skin or lips in this embodiment), LN is a border line between the soft tissue area AN and a part where object O doesn't exist (skin surface line of a human head in this embodiment), FN is a soft tissue filter for executing gradation process of the soft tissue area AN, Fna is a cut-out conceptually provided in the soft tissue filter in order to prepare a part where gradation process is executed and a part where gradation process is not executed. The image in this cut-out area is an X-ray image wherein gradation process is not executed.

In this image, because projection under controlling scan speed, projection under controlling irradiation output or projection under controlling both of them is executed conceptually, the border line LN of the soft tissue area AN is slightly seen (shown with dotted line in the figure) as shown in the cut-out area FNa comparing with a projection without executing such controls.

The image data in the soft tissue filter FN are emphasized against the X-ray image by the filter FN shown in the figure depending on the position of the gradation process standard point P obtained by the position detection means 7, namely gradation process for the soft tissue area AN is executed, the border line LN of the soft tissue area AN is more clearly displayed as shown with solid line in the figure.

The image after filter gradation process is shown in the figure, however, gradation process for the soft tissue area without using the above-mentioned filter, namely gradation process depending on the scan speed of X-ray slit beams and/or irradiation output thereof, may be executed.

A part where X-ray slit beams of which the scan speed and the irradiation output are controlled before irradiation in order to improve its dynamic range are radiated is a part where an X-ray absorption coefficient is different, namely a part where gradation of the X-ray image is different. To which part gradation process should be executed can be determined depending on the scan speed data and the irradiation output data. Utilizing this, the dynamic range is further improved by additionally executing gradation process for the X-ray image after projection, thereby obtaining an X-ray image which can clearly comprehend both the soft tissue area and the hard tissue area.

If both of the above-mentioned gradation process and the filter gradation process are combined, larger effect of dynamic range improvement can be achieved.

A gradation process graph is shown at the bottom of FIG. 4, wherein the reference characters G, G' are a soft tissue area, H is a hard tissue area. Any one of gradation process patterns Q, R, S is selected depending on the output of the X-ray detector 2, namely the X-ray transmitted amount. Alternatively, one of the gradation process patterns Q, R, S may be selected depending on an expected X-ray transmitted amount depending on general control patterns as already explained.

Further, the gradation process pattern Q, R, S can be selected by a selection switch in advance depending on the object's size, or it may be automatically controlled depending on the output of the position detection means at the gradation process standard point or it may be selected from ones stored in advance.

The dynamic range extension method by controlling the irradiation amount during X-ray projection and several dynamic range expansion methods such as gradation process after irradiation and filter gradation process, as mentioned above, may be combined in different ways to be used, thereby achieving each effect interactively.

Figure 5A:
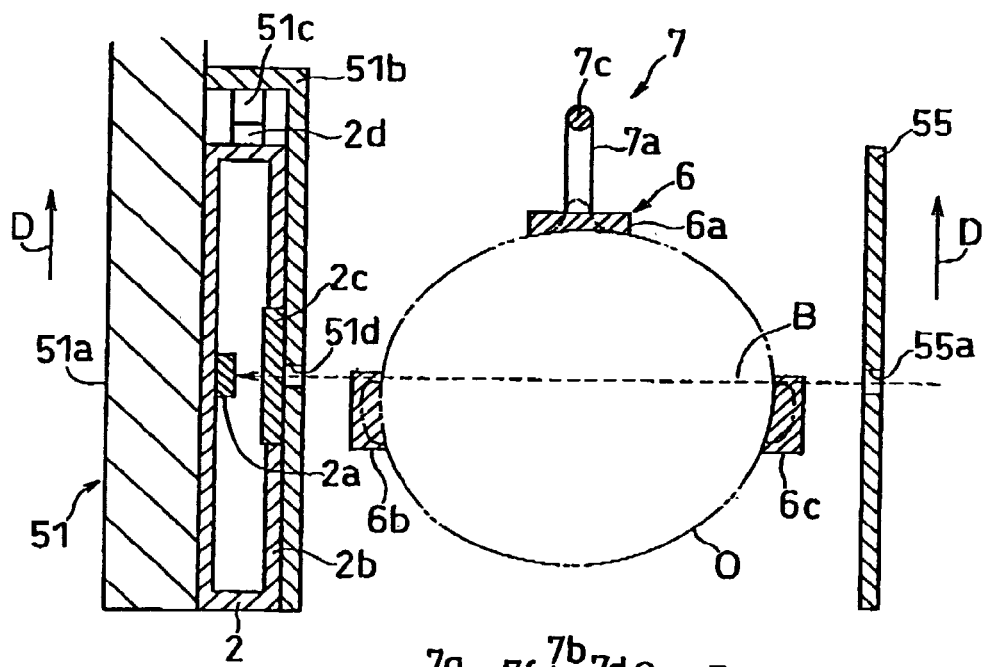
FIG. 5a is a cross-sectional view seen from its top and FIG. 5b is a side view thereof when
Figure 5B:
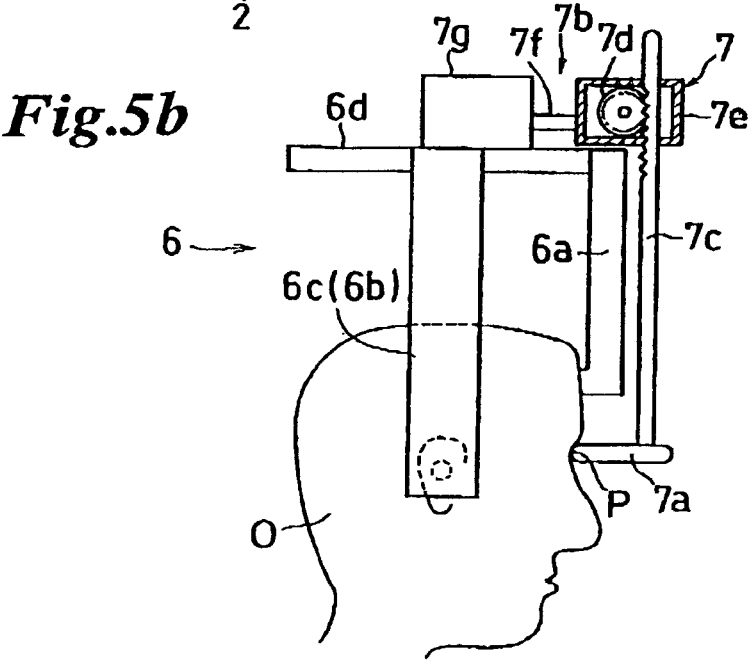

FIG. 5 shows application of the position detection means in FIG. 2, FIG. 5a is a cross-sectional view seen from the top and FIG. 5b is a side view when FIG. 5a is seen from right.

The position detection means 7 is provided for the object fixing means 6 (head fixing means in this embodiment) for fixedly holding object O between the detection holder 51 for detachably supporting the X-ray detector 2 and the secondary slit member 55 having the secondary slit 55a.

The X-ray detector 2 is of cassette type detachably accommodated in the detector holder 51 and is line shape, which has function of converting received transmitted X-rays into electric data and outputting it. Such X-ray detector may include not only so called line sensors but also rectangular shaped sensors with two-dimensional spread as a whole. The X-ray detector 2 comprises an X-ray detection element 2a constructed as a semiconductor detector such as a CCD camera, a case 2b made of an X-ray shielding material in which the X-ray detection element 2a and related control members are accommodated, an X-ray window 2c provided as a window at a part of the case 2b for allowing the transmitted X-rays to be received at the X-ray detection element 2a but shielding visible lights, and a connection portion 2d electrically connected to the detection holder 51 in order to output electrical data that is converted in the X-ray detection element 2a from the transmitted X-ray data.

CCD, CdTe (cadmium tellurium), CdZnTe, CMOS can be used for the X-ray detection element 2a.

If an X-ray detection element such as CdTe having quick response is used, about 150 frame images per a second can be transmitted and moving pictures as well as still images can be constructed. Using several types of dynamic range expansion methods of the present invention, moving pictures comprising clear X-ray images for both the hard tissue area and the soft tissue area can be obtained.

The detection holder 51 is provided with a holder body 51a movably supported for a detector moving axis 52 capable of adjusting its speed, a detection guide 51b for detachably supporting and guiding the X-ray detector 2 and a connection 51c for electrically connecting to the X-ray detector 2.

The head fixing means (object fixing means) 6 is composed of a forehead guide 6a for defining the forehead of an object body O, a pair of ear guides 6b and 6c for defining both ears, and a fixing plate 6d from which those guides 6a, 6b and 6c are suspended. The forehead guide 6a is adjustable from side to side and up and down, the ear guides 6b and 6c can adjust the dimension interposing the head being the median line M as its center from side to side and up and down.

A mechanism for opening and closing the ear guides 6b and 6c of the head fixing means 6 from side to side is constructed such that the open and close distance from side to side can be measured. Those guides comprise a left-to-right position detection means of the position detection means 7 so as to control the scanning speed and the X-ray irradiation output and to execute gradation process depending on the output of the left-to-right position detection means.

A position detector 7b for detecting the position of a contacting detector 7a of the position detection means 7 has a vertical rod 7c, a position detection gear 7d engaging the rod 7c, a vertical position detector 7e accommodating the gear 7d, a back-and-forth moving rod 7f providing with the vertical position detector 7e at its tip end, and a back-and-forth position detector 7g accommodating the rod 7f. The detector 7g is fixed to the fixing plate 6d of the head fixing means (object fixing means) 6.

The vertical position detector 7e of the position detector 7b detects the up and down position of the vertical rod 7c by the position detection gear 7d and cooperating angle detector (not shown, the so-called potentiometer or the like is used) so as to detect the vertical position of the contacting detector 7a. The back-and-forth detector 7g detects the position of the back-and-forth rod 7f in a back and forth direction by detecting the back-and-forth detector 7e in a back and forth direction so that the position of the contacting detector 7a in a back and forth direction is detected.

According to such a construction, the position detection means 7 can easily and accurately detect the position of the gradation process standard point P only by touching the contacting detector 7a on the gradation process standard point P of object O.

According to such position detection means 7, the vertical position is determined as a position in an up and down direction on the basis of a human head O comprising an object, the back-and-forth position is a position in a back and forth direction thereof, and the left-to-right position is determined as a position from side to side thereof.

As for the left-to-right position, when the human head O (object) is fixed with the head fixing means (object fixing means) 6, the median line M agrees with the center of the head fixing means 6. By according the center to the center of the position detector 7b, the size of the interposed human head can be measured by the position of the nasion P (gradation process standard point) where the contacting detector 7a is always on the center of the human head O and by the above-mentioned left-to-right position measuring means. According to this output, the scanning speed and the X-ray irradiation output can be controlled and a gradation process can be executed.

Figure 6:
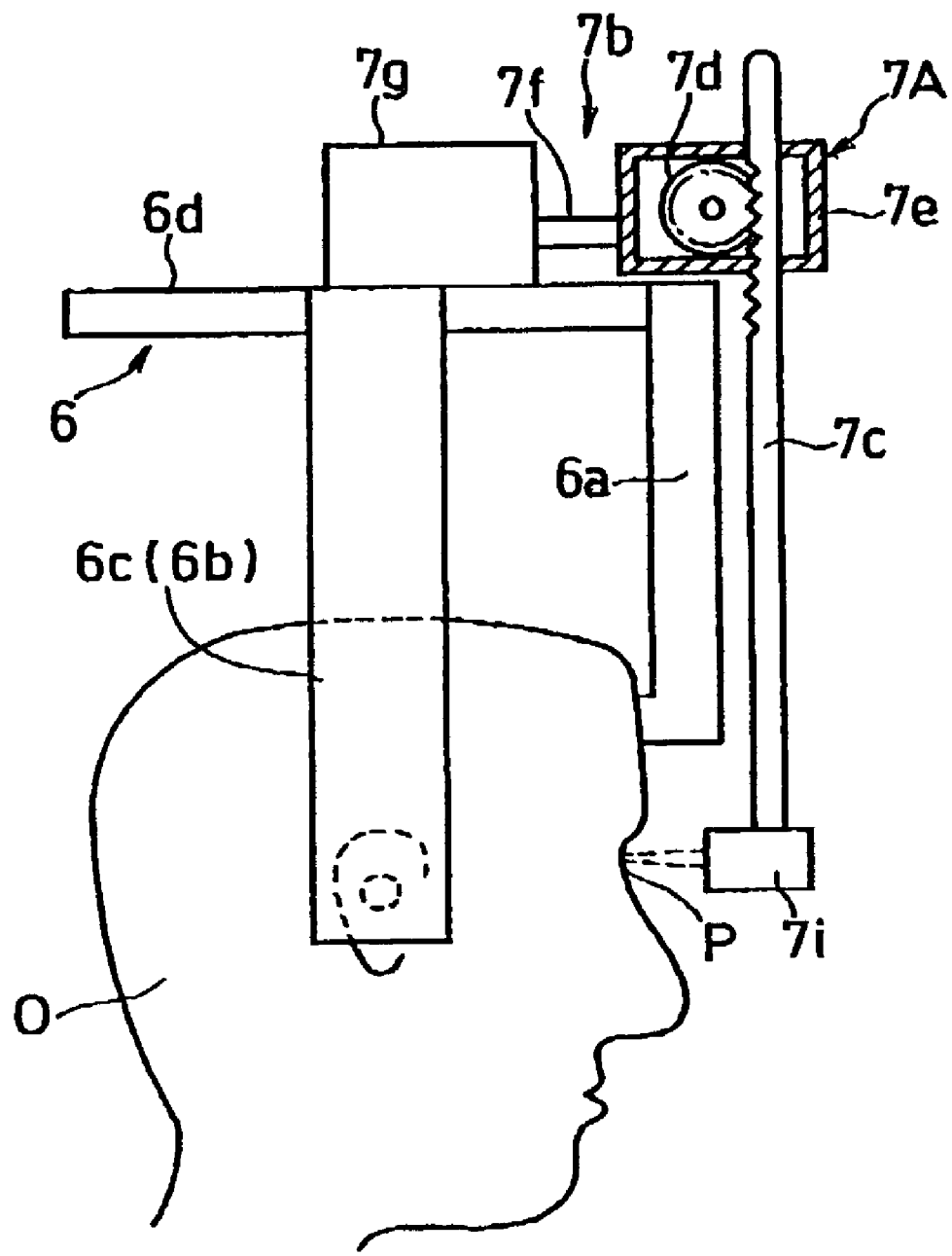
FIG. 6 is a side view of other embodiment of a position detection means used in the present invention.

FIG. 6 is a side view of another embodiment of a position detection means according to the present invention.

The position detection means 7A is different from the position detection means 7 in FIG. 5 in that a non-contacting detector 7i is provided instead of the contacting detector 7a.

The non contacting detector 7i is composed of a well-known range sensor using an infrared light and a visible light and catches the gradation process standard point P at a predetermined position so as to detect the position of the gradation process standard point P of the object.

In case of an infrared light, for example, visible light rays are also used as a guide light and the position of the gradation process standard point P is detected in such a manner that the distance between the non contacting detector 7i and the gradation process standard point P is set at a predetermined distance by an infrared light while keeping a spot illumination by the visible light on the gradation process standard point P. Or in case of a visible light, the position of the gradation process standard point P is detected in such a manner that a predetermined image is clearly produced when the gradation process standard point P comes to its focal position.

Accordingly, the detector does not touch the patient's head so that the position of the gradation process standard point P can be detected without giving a patient unpleasant feeling.

Figure 7:
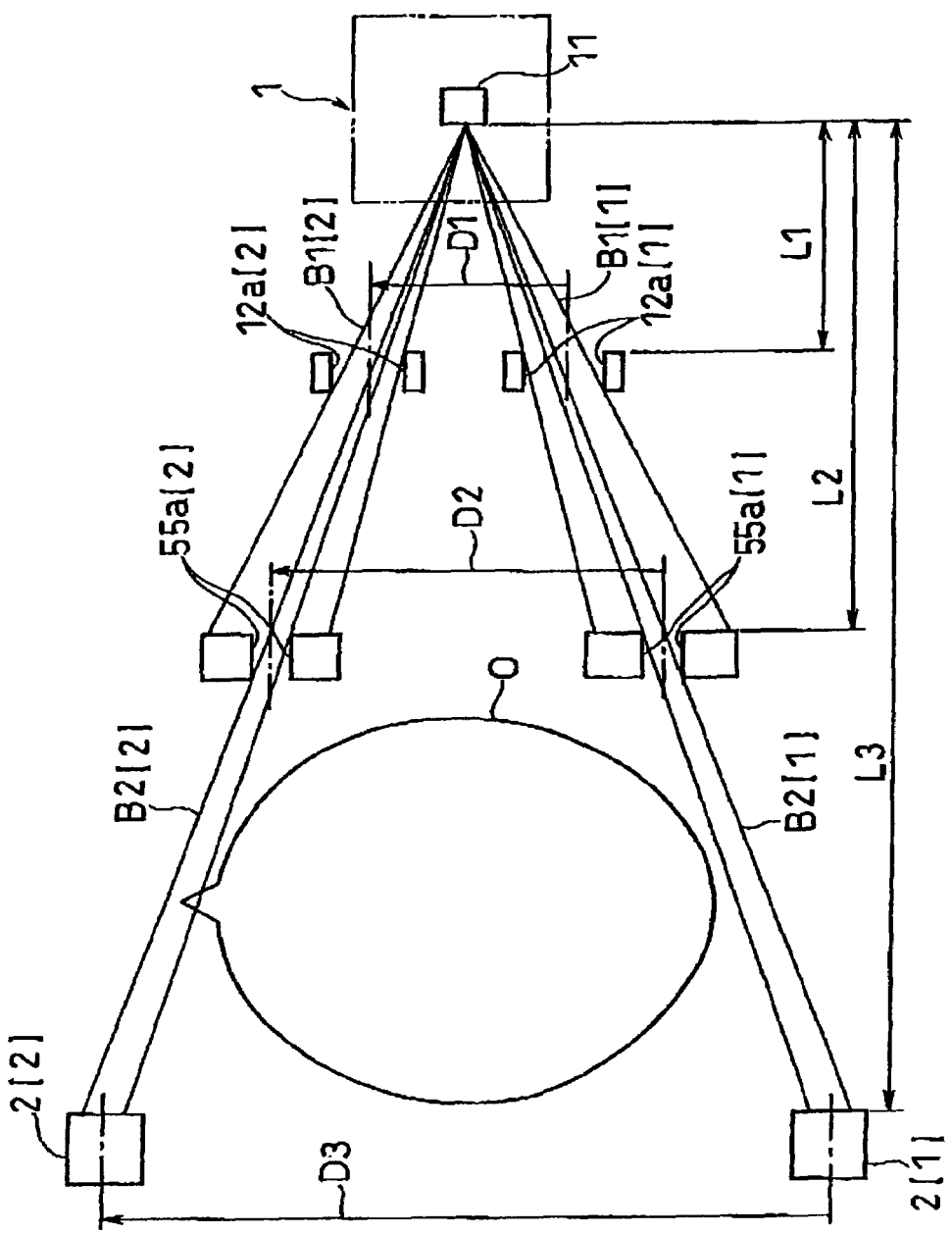
FIG. 7 is an explanatory view of one embodiment of X-ray slit beam scanning according to the scan type digital X-ray imaging apparatus shown in FIG. 1.

FIG. 7 is an explanatory view of one embodiment of X-ray slit beam scanning according to the scan type digital X-ray imaging apparatus shown in FIG. 1. Now a scanning method of X-ray slit beams is explained referring to FIG. 7.

In the figure, the numerals [1] and [2] written after each reference numerals indicate its initial position and its finish position of synchronous movement respectively. The X-ray slit beams B1 indicate slit beams formed by a primary slit 12a and the X-ray slit beams B2 indicate slit beams formed by a secondary slit 55a.

It goes without saying that these X-ray slit beams B1 and B2 are longitudinally narrow beams having a length from the top of a head to the lower part of a jaw.

The reference numeral D1 is a moving distance in a synchronous movement direction D between the centerline of the initial positions [1] of the primary slit 12a and the centerline of the finish positions [2] of the primary slit 12a. Similarly the reference numeral D2 is a moving distance in a synchronous movement direction D between the initial position [1] to the finish position [2] of the secondary slit 55a. Further, the reference numeral D3 is a moving distance in a synchronous movement direction D between the initial position [1] to the finish position [2] of the X-ray detector 2.

The reference numeral L1 is a distance showing the position of the primary slit 12a in a center line direction of the X-ray slit beams B beginning at the fixed X-ray tube 11, L2 is a distance similarly showing the position of the secondary slit 55a and L3 is a distance similarly showing the position of the X-ray detector 2.

Next with reference to this figure, X-ray scanning condition will be given. In such condition it is required that X-ray slit beam emitted at the X-ray generator and then transmitted through an object is always received at the X-ray detector during X-ray scanning while moving the primary slit 12a, the secondary slit 55a and the X-ray detector, with the X-ray tube fixed.

Accordingly in this condition, it requires following relation between distances L1, L2, L3 and moving distances D1, D2, D3.

Distance L1:L2:L3=Moving distance D1:D2:D3

Here, since L1, L2, L3 are constant because they are mechanically fixed, therefore it is required that the slit 12a, the secondary slit 55a, and the X-ray detector 2 may be synchronously moved so as to always establish the above equation.

In such a manner, the X-ray tube 11 which is a irradiation center is fixed so that irradiation and scan of the X-ray slit beams B without runout of its center can be executed, whereby clear X-ray images are obtained.

Figure 8A:
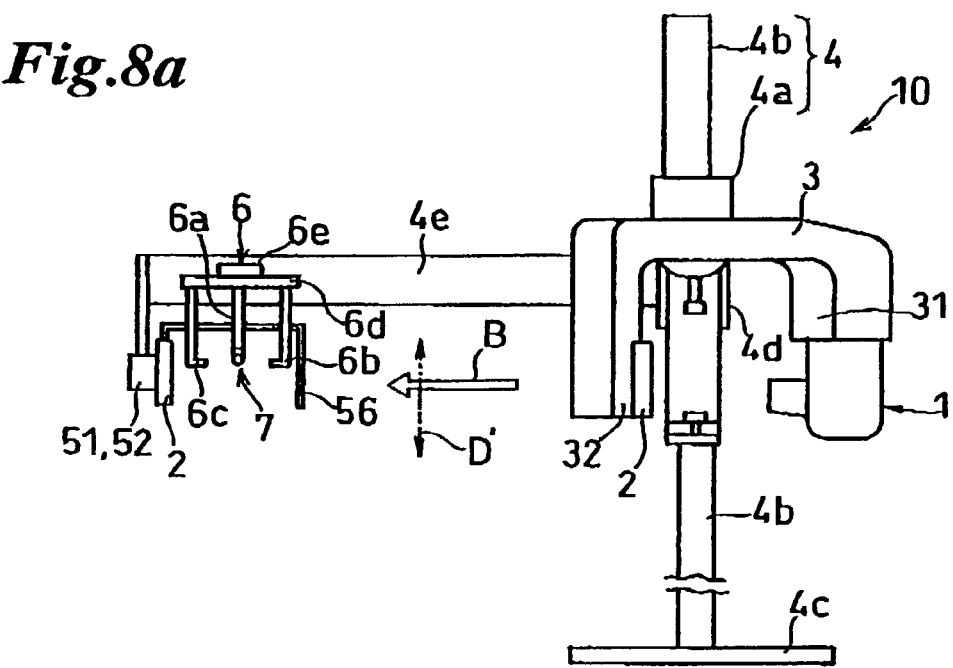
FIG. 8a is its front view and FIG. 8b is its plan view seen from the top.
Figure 8B:
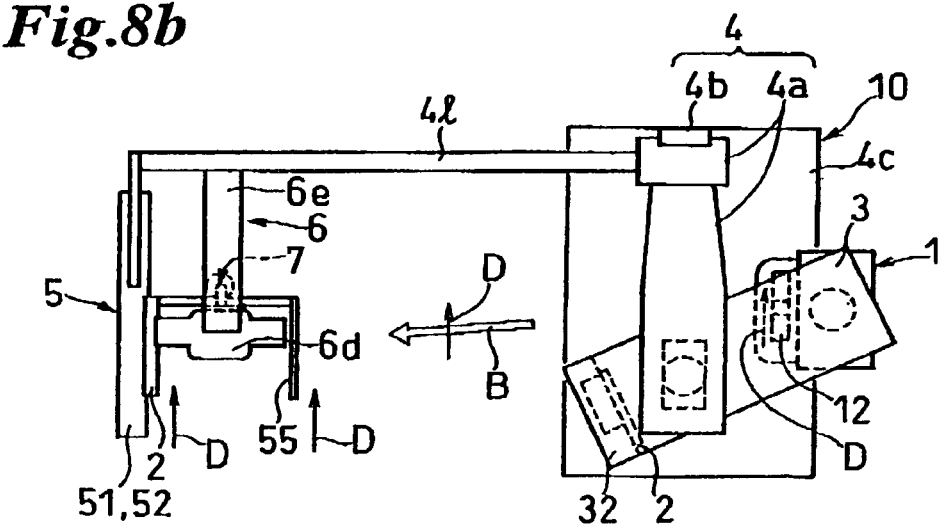

FIG. 8 shows an external view of the scan type digital X-ray imaging apparatus shown in FIG. 1, FIG. 8a is its front view and FIG. 8b is a plan view seen from the top. This apparatus shows an embodiment wherein the present invention is applied for a panoramic X-ray imaging apparatus having a digital cephalometric imaging function.

The dental panoramic X-ray imaging apparatus 10 is provided with a rotary arm from both ends of which a generator holder 31 for rotatably supporting the X-ray generator 1 and the detection holder 32 for detachably supporting the X-ray detector 2 and with a structure 4 for supporting the entire apparatus in addition to the members as explained in FIG. 1.

The structure 4 has a vertical arm 4a for rotatably supporting the rotary arm 3, a brace 4b for supporting the vertical arm 4a so as to be adjustable up and down, a pedestal 4c erecting the brace 4b, an object body fixing means for panoramic radiography 4d for fixing the object around the rotation center of the rotary arm 3, the fixing means 4b suspending from the vertical arm 4a, and an arm for cepharometric radiography 4e extended from the vertical arm 4a in a crosswise direction.

According to this object body fixing means 6, the rotary arm 3 comes to a rotary angle position at the end of the arm for cepharometric radiography 4e as shown in the plan view of FIG. 8b, and the line connecting the X-ray generator 1 suspended from the arum 3 and the object fixing means 6 is positioned so as to be substantially parallel with the arm for cepharometric radiography 4e and so as to be where the distance between the object fixing means 6 and the X-ray generator 1 becomes a predetermined distance for cepharometric radiography via the horizontal arm 6e.

According to the dental panoramic X-ray imaging apparatus 10 thus constructed, the object is fixed to the object fixing means 6 and on the other hand the X-ray generator 1 is fixed as shown in the figure. The primary slit member 12, the secondary slit member 55, and the X-ray generator 2 are synchronously moved to scan with the X-ray slit beams B, thereby executing a cepharometric radiography of the human head, an object to be radiographed. Further, as mentioned above, the scanning speed and the irradiation output of the X-ray slit beams B can be controlled depending on the X-ray transmitted amount sequentially received in the X-ray generator 2. Furthermore, gradation process of a soft tissue area is executed on the obtained X-ray images and the X-ray images of which the hard tissue area and soft tissue area have clear images.

The synchronous movement direction D, namely a scan direction D of the X-ray slit beams B, is a horizontal direction perpendicular to the irradiation direction of the X-ray slit beams in this embodiment. However, it may be a vertical direction, namely an up-and-down movement perpendicular to the irradiation direction of the X-ray slit beams like the direction D' shown by an arrow with two dotted line (imaginary line) in the figure.

On the other hand, panoramic radiography can be executed in such a manner that the X-ray generator 1 is directed to the center of the rotation of the rotary arm 3, the X-ray detector 2 is attached to the detection holder 32, the human head which is an object is fixed with the object fixing means 4d, the X-ray generator 1 and the X-ray detector 2 are rotated around the object while facing each other and X-ray slit beams are radiated while moving the rotation center of the X-ray generator 1 and the X-ray detector 2 according to the principle of a well known curved surface tomography method.

The dental panoramic X-ray imaging apparatus 10 can thus execute two kinds of radiography, a panoramic radiography and a cepharometirc radiography without providing an X-ray generator and an X-ray detector separately, thereby saving resource.

Figure 9A:
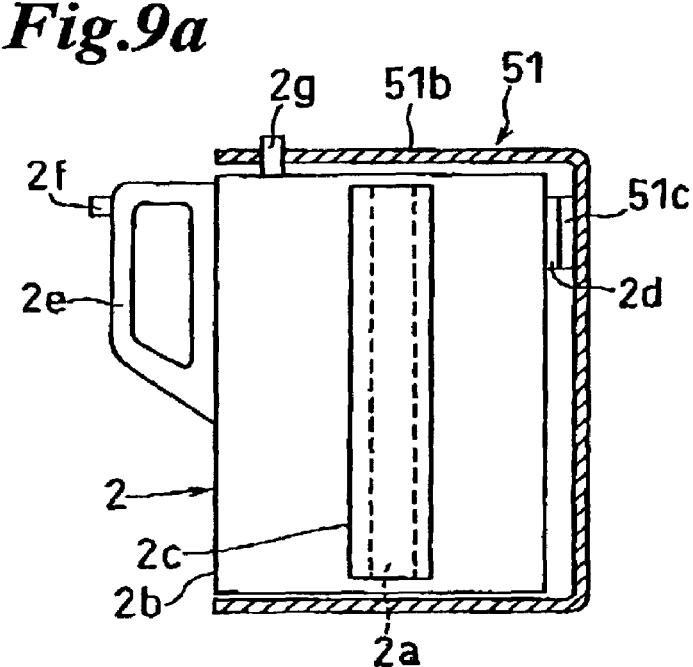
FIG. 9a is a front view in use.
Figure 9B:
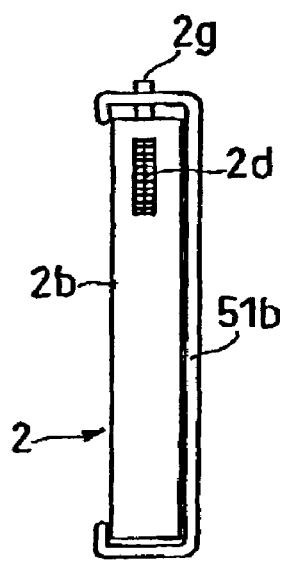
FIG. 9b is a side view of FIG. 9a, and FIG. 9c is a partially enlarged vertical section explaining an engaging mechanism of an X-ray detector.
Figure 9C:
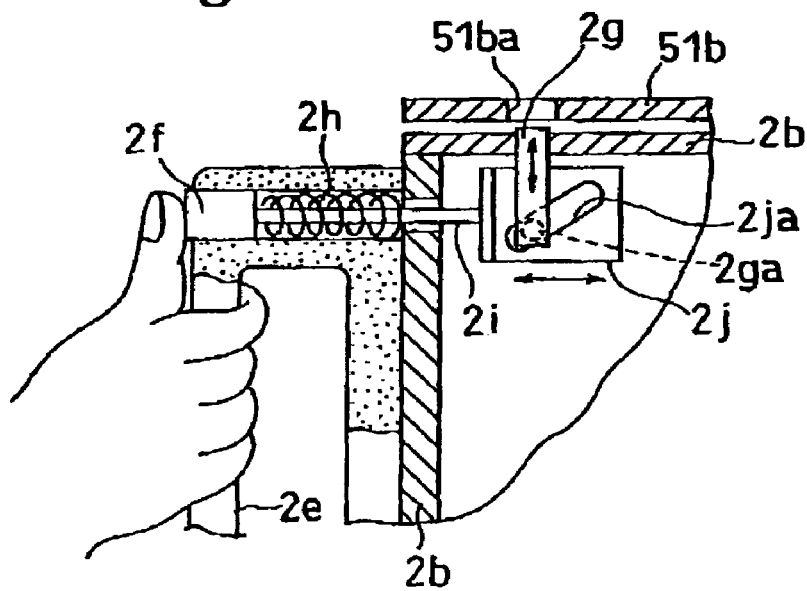

FIG. 9 is a detailed view of the X-ray detector shown in FIG. 1 and so on, FIG. 9a is a front view when it is used, FIG. 9b is a side view of FIG. 9a, and FIG. 9c is a partially enlarged vertical section explaining an engaging mechanism of the X-ray detector.

The X-ray detector of the present invention is applicable to different types of radiographies, namely the detection holder 51 for cepharometric radiography and the detection holder 32 for panoramic radiography, and can be mounted in a one-touch manner. Now, the mechanism for this purpose is explained.

The X-ray generator 2 comprises a grip 2e for holding the detector 2 with one hand, an operation button 2f capable of pushing with a thumb of one hand holding the grip 2e, and an engage pin 2g wherein the operation button 2f is pushed, then the pin 2g is accommodated as shown in FIG. 9c and when the thumb is removed from the button 2f, the pin 2g is projected out of the top of the case 2b as shown in FIG. 9a and FIG. 9b.

The operation button 2f is provided with a crank plate 2j formed of a shaft 2i and a crank groove 2ja provided at the tip of the shaft 2i. A spring 2h is outwardly inserted in the shaft 2j so as to give elasticity to keep the operation button 2f projected from the grip 2e in a normal condition. A slide pin 2ga is provided under the engage pin 2g so as to slidably fit in the crank groove 2ja of the crank plate 2j.

The crank groove 2ja of the crank plate 2j is so designed as to be able to move the slide pin 2ga engaged in the crank groove 2ja up and down when the operation button 2f is slid in a horizontal direction in the figure.

According to such a construction, when the X-ray detector 2 is attached to the detection holder 51, the X-ray detector 2 is engaged in a detector guide 51b while the grip 2e is held with one hand and the operation button 2f is pushed. After pushing until a connection part 2d of the X-ray detector 2 and a connection part 51c of the detection holder 51 are naturally combined and connected, the operation button 2f is released and the hand holding the grip 2e is released, operation condition becomes as shown in FIG. 9a and FIG. 9b so that the X-ray detector 2 and the detection holder 51 are detachably connected in one step.

For removing the X-ray detector 2, the push button 2f is pushed while the grip 2e is held with one hand as shown in FIG. 9c and the detector 2 is pulled. Thus the X-ray detector 2 is easily removed in one step.

A holder guide (not shown) of the other detector holder 32 for attaching the X-ray detector 2 is of the same construction as the holder guide 51b of the detection holder 51 as shown in the figure and is able to attach and detach the X-ray detector 2 in one step, therefore achieving convenience. Further, the same X-ray detector can be easily used for different radiography.

Figure 10:
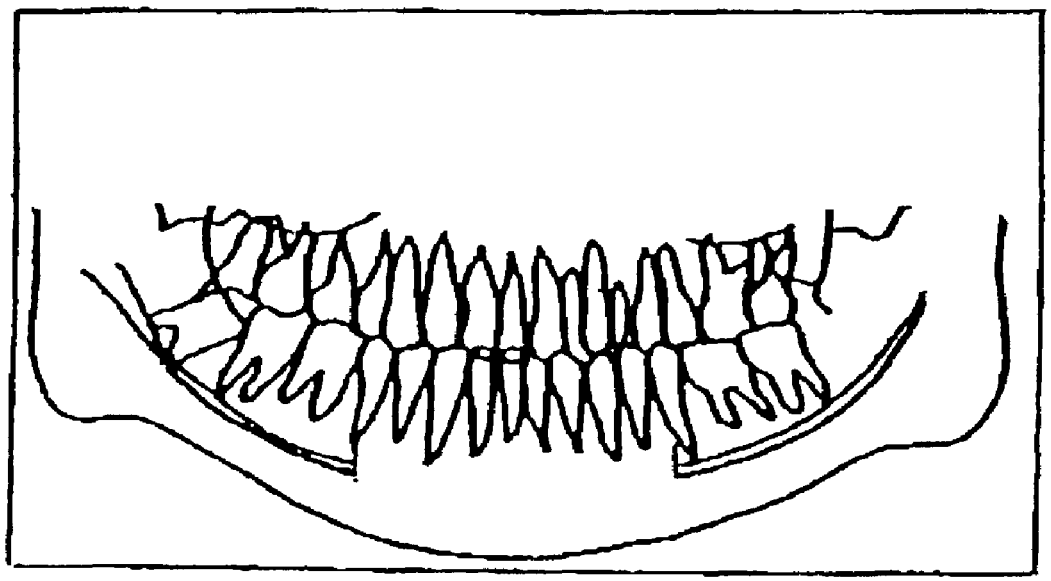
FIG. 10 shows a panoramic radiography capable in the scan type digital X-ray radiography apparatus shown in FIG. 8.

FIG. 10 explains panoramic radiography capable in the scan type digital X-ray radiography apparatus shown in FIG. 8 and shows one example of a panoramic X-ray image obtained by this method.

Panoramic X-ray radiography is already explained with reference to FIG. 8 and according to such a radiography, a panoramic X-ray image of a dental jaw can be obtained as shown in FIG. 10.

Figure 11A:
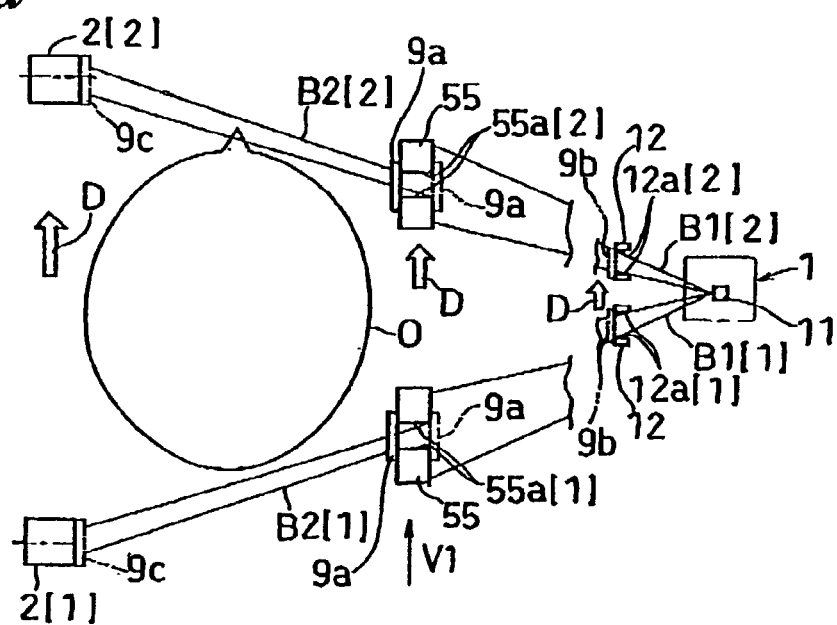
FIG. 11a is an explanatory view showing one embodiment of a scanning pattern of the X-ray slit beam when a vertical filter is used for a scan type digital X-ray imaging apparatus of the present invention.
Figure 11B:
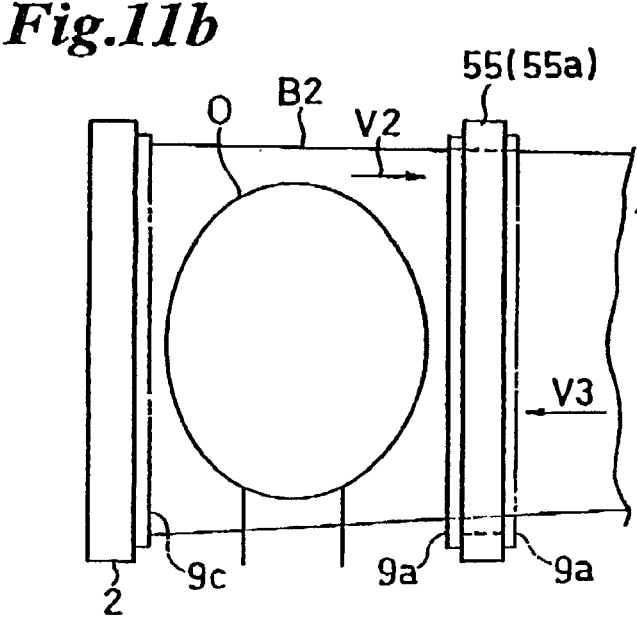
FIG. 11b is a fragmentary view in a direction of arrow V1.
Figure 11C:
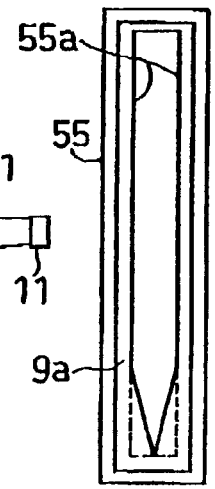
FIG. 11c is a fragmentary view in a direction of arrow V2.

FIG. 11a is an explanatory view showing one embodiment of a scanning pattern of the X-ray slit beam when a vertical filter is used for a scan type digital X-ray imaging apparatus of the present invention, FIG. 11b is a fragmentary view in a direction of arrow V1, FIG. 11c is a fragmentary view in a direction of arrow V2, FIG. 12a is an explanatory view of an X-ray image obtained without using the vertical filter and FIG. 12b is an explanatory view of an X-ray image obtained using the vertical filter. FIG. 12a is a fragmentary view in a direction of arrow V3 in FIG. 11b.

FIG. 11a is different from the scan type digital X-ray imaging apparatus explained in FIG. 7 in that a vertical filter 9a is provided at an object O side of a secondary slit member 55 so as to cover a secondary slit 55a.

The vertical filter 9a is made of radiopaque material such as lead and its lower part of the rectangular secondary slit 55a in the figure is narrowed like a wedge as shown in FIG. 11.

Therefore, the X-ray slit beam reached the object from the secondary slit 55a has the same beam width (width in scanning direction of X-ray slit beam B) where the width of the secondary slit 55a isn't controlled by the vertical filter 9a, on the other hand the beam width is gradually narrowed where the width of the secondary slit 55a is controlled by the vertical filter 9a.

When the X-ray slit beam B having different sectional areas in vertical direction scans the object, the irradiation is made due to the amount of time corresponding to the beam width at the area of the X-ray slit beam B with different beam width. At the area, an irradiation energy of the X-ray slit-beam is reduced corresponding to the beam width.

FIG. 12 is a comparison of the X-ray image (a) obtained without using the vertical filter 9a and the X-ray image (b) obtained using the vertical filter 9a. As shown in this comparison, the area under a chin of a soft tissue AN of the object O is shown with a dotted line, thereby the image isn't clear in FIG. 12a, however, in FIG. 12b it can be seen in a solid line and the image is clear.

Thus the irradiation energy of the X-ray slit beam B is controlled in up and down direction (vertically) and the X-ray slit beam B is radiated, clear images of the area where the hard tissue area and the soft tissue area exist separately in vertical direction can be obtained corresponding to each tissue area.

That is to say, the irradiation energy of the X-ray slit beam B is changed, namely controlled, in scanning direction, namely in a right angle against a synchronizing direction for synchronously moving the X-ray slit beam radiated from the X-ray generator and the X-ray detector in the same direction, clear images can be obtained for both a hard tissue area and a soft tissue area by enlarging the dynamic range of X-ray imaging for the object in which the change from a hard tissue area to the soft tissue area is caused in a right angle (vertical direction) against the synchronous movement (scanning direction).

This vertical filter 9a may be provided for the secondary slit member 55 at the opposite side to the object as shown in chain double-dashed lines in FIG. 11a, for the object side of the primary slit member 12, or for the opposite side to the object of the primary slit member 12. The vertical filter 9b provided for the primary slit member 12 is formed smaller corresponding to the shape of the primary slit 12a.

Further, the vertical filter 9c may be provided for a light receiving face of the X-ray detector 2 as shown in chain double-dashed lines in FIG. 11a. In this case, the irradiation energy of the X-ray slit beam B transmitted through the object O is changed into a direction normal to the synchronous movement. In this way, clear images can be also obtained for both a hard tissue area and a soft tissue area by enlarging the dynamic range of X-ray imaging for the object in which the change from a hard tissue area to the soft tissue area is caused in a right angle (vertical direction) against the synchronous movement.

Still further, the vertical filters 9a, 9b and 9c can be provided in combination.

In addition, when the vertical filters 9a, 9b and 9c are moved while emitting the X-ray slit beam B, they can correspond to the area where the change between a hard tissue area and a soft tissue area is caused oblique, other than the case the change is caused up and down.

The vertical filters 9a, 9b and 9c are designed to be detachably attached to the primary slit member 12, the secondary slit member 55 and the X-ray detector 2 which are objects to be attached, therefore, they may be removed if unnecessary or may be attached depending on the object.

Moreover, the vertical filters 9a, 9b and 9c may be fixedly provided for the primary slit member 12, the secondary slit member 55 and the X-ray detector 2.

Figure 13:
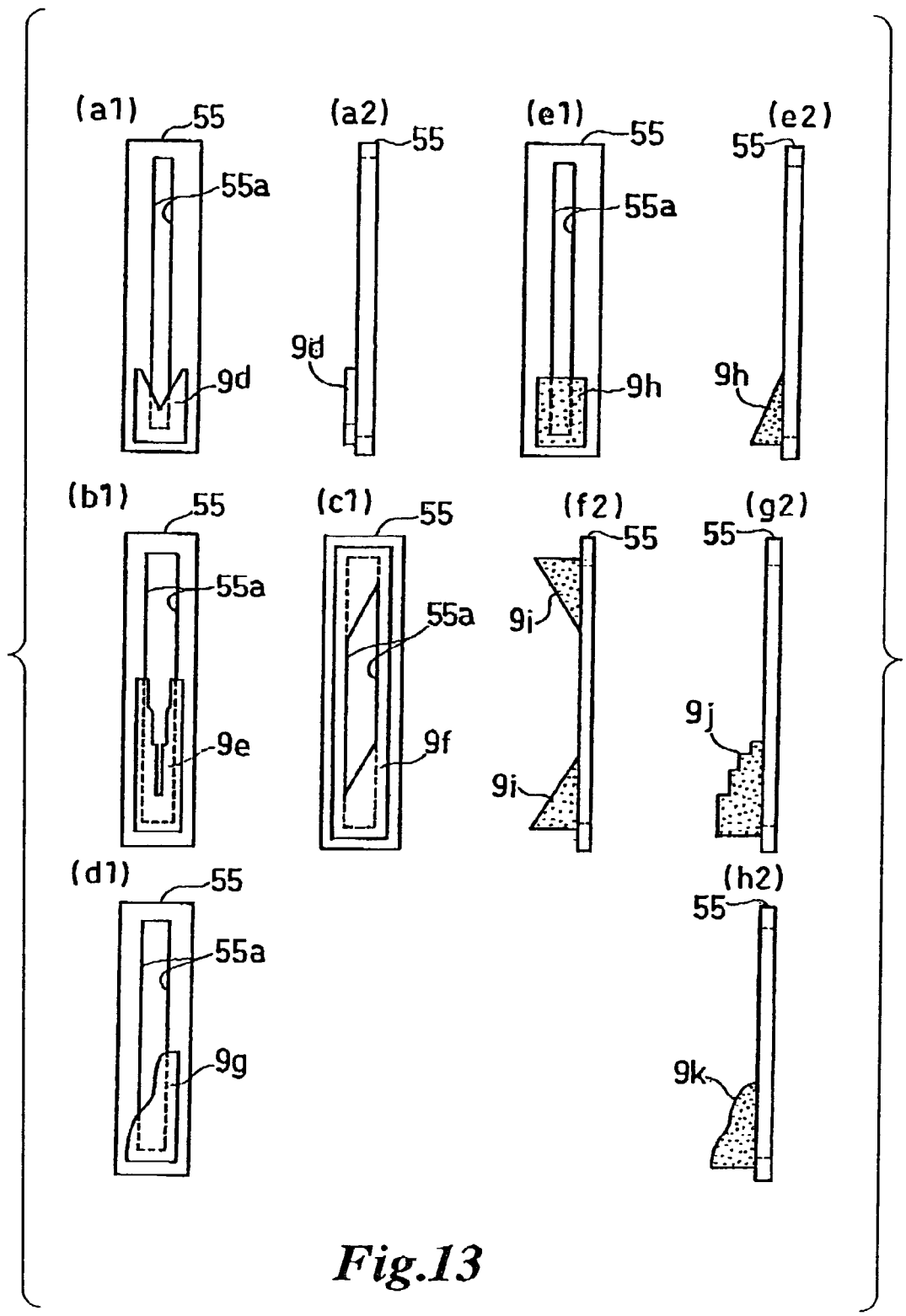
FIG. 13 shows several kinds of vertical filters provided for the secondary slit member.
Figure 14A:
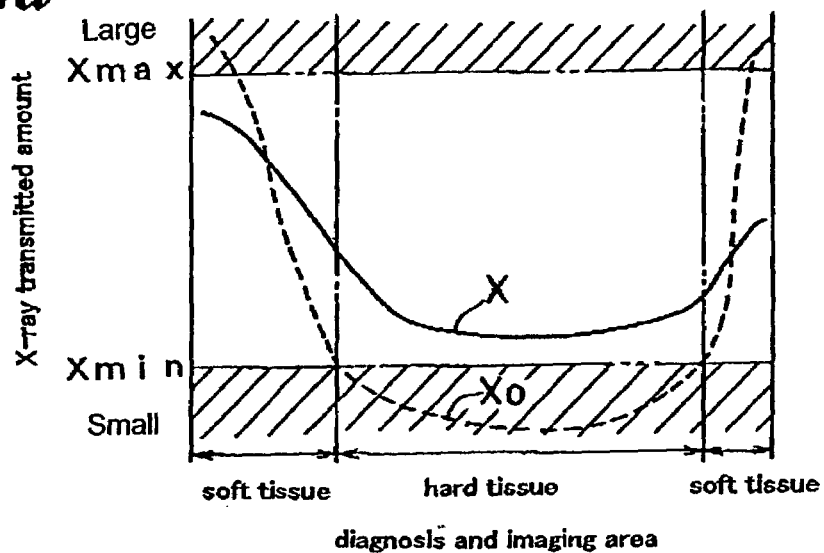
FIG. 14a shows a graphic showing a relation between the imaging area and the X-ray transmitted amount and FIG. 14b is a graphic showing a relation between the imaging area and the scanning speed of an X-ray slit beam when the head of an object is examined using the apparatus of the present invention.
Figure 14B:
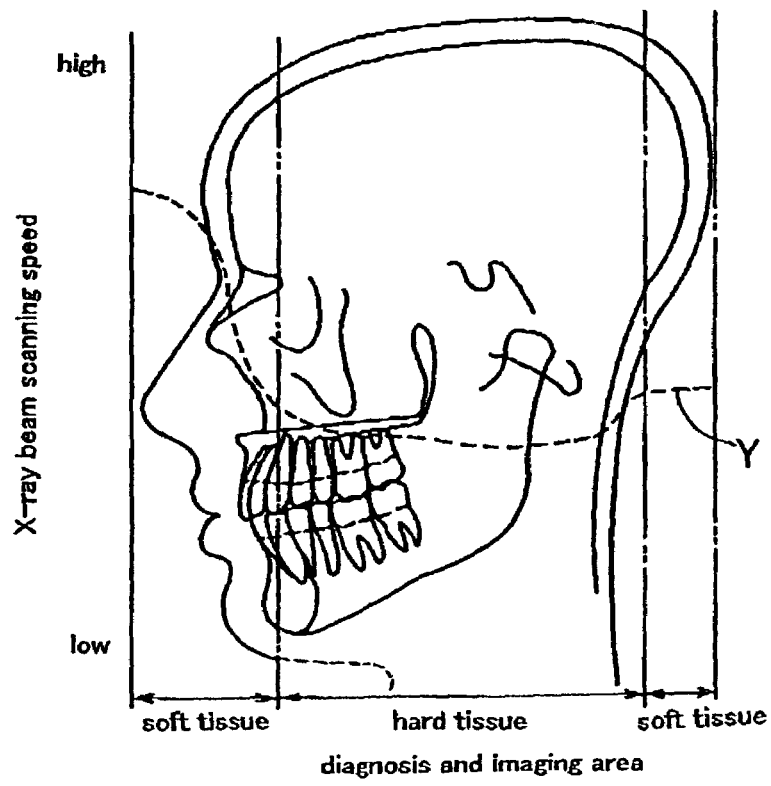

FIG. 13 shows several kinds of vertical filters provided for the secondary slit member. FIG. 13a1, FIG. 13b1, FIG. 13c1, FIG. 13d1 and FIG. 13e1 are front views and FIG. 13a2, FIG. 13e2, FIG. 13f2, FIG. 13g2 and FIG. 13h2 are its side views respectively.

In the figure, the front views, FIG. 13a1, FIG. 13b1, FIG. 13c1, FIG. 13d1 and FIG. 13e1, are fragmentary views of FIG. 11b in a direction of arrow V2. The side views, FIG. 13a2, FIG. 13e2, FIG. 13f2, FIG. 13g2 and FIG. 13h2, are fragmentary views of FIG. 11a in a direction of arrow V1.

The vertical filters 9d, 9e, 9f and 9g shown in FIG. 13a1, FIG. 13a2, FIG. 13b1, FIG. 13c1 and FIG. 13d1 are made of radiopaque material like the vertical filter 9a in FIG. 12 and control the opening of the secondary slit 55a by its shape. Several types of wedge may be used according to the object. The wedge may be formed at a necessary part like the vertical filter 9d, formed like a staircase pattern such as the vertical filter 9e, formed at its top and bottom and only one side is inclined like the vertical filter 9f, or formed in a curve like the vertical filter 9g.

The vertical filters 9h, 9i, 9j and 9k shown in FIG. 13e1, FIG. 13e2, FIG. 13f2, FIG. 13g2 and FIG. 13h2 are made of X-ray semi-permeable material having a certain X-ray semi-permeable property, unlike those mentioned above, made of radiopaque material.

In this case, for changing the irradiation energy of the X-ray slit beam b into perpendicular against the synchronous direction (scanning direction), the thickness of the X-ray semi-permeable material in a direction of X-ray slit beam B irradiation is changed in perpendicular (up and down direction, vertical direction).

In this manner, the same effect as the vertical filters 9a-9g can be obtained and the change of thickness in up and down direction can be varied like the vertical filters 9h, 9i, 9j and 9k.

In this invention, several types of filters having a filter function including the above mentioned ones are called as a vertical filter.

Further, in the above-mentioned embodiment a patient stands up or sits on a chair in a vertical direction while being scanned, however, the patient may lay on a horizontal bed like a CT imaging apparatus.

The invention claimed is:

1. A scan type digital X-ray imaging apparatus comprising an X-ray generator for emitting X-ray slit beams, an X-ray detector for detecting X-ray transmitted through an abject to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray generator for said object and is received on said X-ray detector, with said X-ray generator still relative to said object, while said X-ray slit beam and said X-ray detector are synchronously moved in the same direction with said object interposed therebetween, thereby producing an X-ray image of the object, and wherein a scanning speed of said X-ray slit beam is feedback controlled such that an X-ray transmitted amount of said X-ray slit beams through said object detected by said X-ray detector provides an appropriate photographic density for both a soft tissue and a hard tissue region in said object, depending on the X-ray transmitted amount, whereby said scanning speed of the X-ray slit beam becomes faster for a soft tissue region in said object than for a hard tissue region in said object.

2. The scan type digital X-ray imaging apparatus as set forth in claim 1, wherein plural kinds of standard data of pulse rate for feedback controlling the scanning speed of the X-ray slit beam are stored in advance corresponding to the regions to be examined in said object.

3. A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray generator for said object and is received on said X-ray detector, with said X-ray generator still relative to said object, while said X-ray slit beam and said X-ray detector are synchronously moved in the same direction with said object interposed therebetween, thereby producing an X-ray image of the object, and wherein an output intensity of the X-ray slit beam is feedback controlled such that an X-ray transmitted amount of said X-ray slit beams through said object detected by said X-ray detector provides an appropriate photographic density for both a soft tissue and a hard tissue region in said object, depending on the X-ray transmitted amount, whereby said output intensity of the X-ray slit beam becomes smaller for a soft tissue region in said object than for the hard tissue region in said object.

4. A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray generator for said object and is received on said X-ray detector, with said X-ray generator still relative to said object, while said X-ray slit beam and said X-ray detector are synchronously moved in the same direction with said object interposed therebetween, thereby producing an X-ray image of the object, and wherein a control pattern for controlling a scanning speed of said X-ray slit beams is prepared in advance based on an expected X-ray transmitted amount which passes through a soft tissue and a hard tissue of the object, said expected X-ray transmitted amount being such value as to be appropriate for photographic density for both a soft tissue and a hard tissue region in said object, depending on positions of said object where X-ray absorption coefficient of said object fixed with said object fixing means is changed, whereby said scanning speed of the X-ray slit beam becomes faster for a soft tissue region in said object than for a hard tissue region in said object.

5. The scan type digital X-ray imaging apparatus as set forth in claim 4, wherein the output intensity of said X-ray slit beam is further controlled while controlling the scanning speed of said X-ray slit beam.

6. A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray generator for said object and is received on said X-ray detector, with said X-ray generator still relative to said object, while said X-ray slit beam and said X-ray detector are synchronously moved in the same direction with said object interposed therebetween, thereby producing an X-ray image of the object, wherein a control pattern for controlling the output intensity of said X-ray slit beams is prepared in advance based on an expected X-ray transmitted amount which passes through a soft tissue and a hard tissue of the object, said expected X-ray transmitted amount being such value as to be appropriate for photographic density for both a soft tissue and a hard tissue region on said object, depending on positions of said object where X-ray absorption coefficient of said object fixed with said object fixing means is changed, wherein said output intensity of the X-ray slit beam is controlled depending on said control pattern, whereby the output intensity of the X-ray becomes smaller for a soft tissue region in said object than for a hard tissue region in said object.

7. A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning performed in a manner that the X-ray silt beam is emitted from said X-ray generator for said object while said X-ray slit beam and said X-ray detector are synchronously moved in the same direction with said object interposed therebetween, thereby producing an X-ray image of the object, and wherein said X-ray apparatus comprises a position detection means for detecting a reference point of gradation processing for said object, depending on an expected X-ray transmitted amount prepared in advance for said object fixed with said object fixing means and based on said reference point detected by said position detection means, the pulse rate of a pulse motor for scan driving is changed, and the scanning speed of said X-ray slit beam is controlled to be faster for a soft tissue region in said object than for a hard tissue region in said object, and wherein said expected X-ray transmitted amount is preset at such a desired control level as to satisfy an appropriate photographic density for both a soft tissue and a hard tissue region in said object, respectively.

8. The scan type digital X-ray imaging apparatus as set forth in claim 7, wherein the output intensity of said X-ray slit beam is further controlled while controlling the scanning speed of said X-ray slit beam.

9. A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray generator for said object while said X-ray slit beam and said X-ray detector are synchronously moved in the same direction with said object interposed therebetween, thereby producing an X-ray image of the object, and wherein said X-ray apparatus comprises a position detection means for detecting a reference point of gradation processing for said object, depending on an expected X-ray transmitted amount prepared in advance for said object fixed with said object fixing means and based on said reference point detected by said position detection means, the pulse intensity of said X-ray slit beam is controlled, and wherein said expected X-ray transmitted amount is preset at such a desired control level as to satisfy an appropriate photographic density for both a soft tissue and a hard tissue region in said object, respectively.

10. A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray slit beam for said object while said X-ray generator and said X-ray detector are synchronously moved in the same direction with said object interposed therebetween, thereby producing an X-ray image of the object, and wherein after said X-ray beam scanning, a gradation of said X-ray image produced by said X-ray detector is controlled by selecting a different gradation process pattern for a soft tissue region and a hard tissue region in said object respectively depending on the scanning speed and/or the output intensity of said X-ray slit beam having been scanned for said object.

11. A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray generator for said object while said X-ray slit beam and said X-ray detector are synchronously moved in the same direction with said object interposed therebetween, thereby producing an X-ray image of the object, and wherein after said X-ray beam scanning, said X-ray image produced by said X-ray detector is controlled its gradation by selecting a different gradation process pattern for a soft tissue region and a hard tissue region in said object respectively depending on the X-ray transmitted amount having been detected by said X-ray detector during X-ray beam scanning.

12. A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray generator for said object while said X-ray slit beam and said X-ray detector are synchronously moved in the same direction with said object interposed therebetween, thereby producing an X-ray image of the object, and wherein an X-ray image produced by said X-ray detector is controlled its gradation by selecting a different gradation process pattern for a soft tissue region and a hard tissue region in said object respectively depending on said expected X-ray transmitted amount prepared in advance according to said object fixed with said object fixing means.

13. A scan type digital X-ray imaging apparatus comprising an X-ray generator for emitting X-ray slit beams, an X-ray detector for detecting X-ray transmitted through an object to be examined, and an object fixing means disposed between the X-ray generator and the X-ray detector, for holding the object in an appropriate position for X-ray photography, in which X-ray beam scanning is performed in a manner that the X-ray slit beam is emitted from said X-ray slit beam for said object while said X-ray generator and said X-ray detector are synchronously moved in the same direction with said object interposed therebetween, thereby producing an X-ray image of the object, and wherein said X-ray imaging apparatus further comprises a reference point detection means for detecting a reference point of gradation processing for said object, and wherein said X-ray image produced by said X-ray detector is controlled its gradation by way of filtering gradation by selecting a different gradation process pattern for a soft tissue region and a hard tissue region in said object respectively depending on said reference point of gradation processing detected by said reference point detection means.

14. The scan type digital X-ray imaging apparatus as set forth in claim 13, wherein after said X-ray beam scanning, said X-ray image produced by said X-ray detector is controlled its gradation, depending on a scanning speed and/or an output intensity of X-ray slit beams which have been emitted to said object during said X-ray beam scanning.

15. The scan type digital X-ray imaging apparatus as set forth in claim 1 wherein the output intensity of said X-ray slit beam is further controlled while controlling the scanning speed of said X-ray slit beam.

16. The scan type digital X-ray imaging apparatus as set forth in any one of claims 1, 2, 3, 4, 6, 5, 7, 9 or 8, wherein after said X-ray beam scanning, said X-ray image produced by said X-ray detector is controlled its gradation, depending on the scanning speed and/or the output intensity of said X-ray slit beams which have been emitted to said object during said X-ray beam scanning.

17. The scan type digital X-ray imaging apparatus as set forth in any one of claims 1, 2, 3, 4, 6, 5, 7, 9 or 8, wherein after said X-ray beam scanning, said X-ray image produced by said X-ray detector is controlled its gradation, depending on the X-ray transmitted amount having been detected by said X-ray detector during X-ray beam scanning.

18. The scan type digital X-ray imaging apparatus as set forth in claim 17, wherein a vertical filter is further detachable or secured to said apparatus, said vertical filter changing gradually or stepwisely the irradiation energy of X-ray slit beam normal to said synchronous movement direction.

19. The scan type digital X-ray imaging apparatus as set forth in any one of claims 1, 2, 3, 4, 6, 5, 7, 9 or 8, wherein after X-ray beam scanning, said X-ray image produced by said X-ray detector is controlled its gradation, depending on an expected X-ray transmitted amount according to said object fixed with said object fixing means.

20. The scan type digital X-ray imaging apparatus as set forth in any one of claims 1, 2, 3, 4, 6 or 5, wherein said X-ray imaging apparatus further comprises a reference point detection means for detecting a reference point of gradation processing for said object, and wherein said X-ray image produced by said X-ray detector is controlled its gradation by way of filtering gradation, depending on said reference point of gradation processing detected by said reference point detection means.

21. The scan type digital X-ray imaging apparatus as set forth in any one of claims 1, 2, 3, 4 or 10, wherein said X-ray slit beam and said X-ray detector are synchronously moved with an X-ray tube provided on said X-ray generator fixed thereon, by moving a primary slit provided on said X-ray generator adjacent to said X-ray tube and a secondary slit provided on the X-ray generator side of said object fixing means, together with said X-ray detector in the same direction.

22. The scan type digital X-ray imaging apparatus as set forth in any one of claims 1, 2, 3, 4 or 10, wherein said X-ray detector is composed of a semiconductor detector such as a CCD camera, and wherein said X-ray slit beam and said X-ray detector are synchronously moved relative to said object in an up and down direction normal to the irradiation direction of said X-ray slit beam or in a right or left direction to said irradiation direction of said X-ray slit beam.

23. The scan type digital X-ray imaging apparatus as set forth in any one of claims 1, 2, 3, 4 or 10, wherein said object fixing means is composed of a head fixing means, and wherein said X-ray imaging apparatus is a dental digital cephalometric X-ray imaging apparatus.

24. The scan type digital X-ray imaging apparatus as set forth in any one of claims 1, 2, 3, 4, 10 or 11, wherein a vertical filter is further detachable or secured to said apparatus, said vertical filter changing gradually or stepwisely the irradiation energy of X-ray slit beam normal to said synchronous movement direction.

25. The scan type digital X-ray imaging apparatus as set forth in any one of claims 7 or 9,
wherein said X-ray image produced by said X-ray detector is controlled in its gradation by way of filtering gradation, depending on said reference point of gradation processing detected by said reference point detection means.

26. The scan type digital X-ray imaging apparatus as set forth in claim 25,
wherein a vertical filter is further detachable or secured to said apparatus, said vertical filter changing gradually or stepwisely the irradiation energy of X-ray slit beam normal to said synchronous movement direction.

27. The scan type digital X-ray imaging apparatus as set forth in any one of claims 7, 10 or 13,
wherein said position detection means comprises a contacting detector supported movably and adjustably in its position relative to said object fixing means and wherein said reference point of gradation processing for said object is detected by bringing said contacting detector into contact with said reference point for said object.

28. The scan type digital X-ray imaging apparatus as set forth in any one of claims 7, 10 or 13,
wherein said position detection means comprises a non contacting detector supported movably and adjustably in its position relative to said object fixing means and wherein said reference point of gradation processing for said object is detected by directing said non contacting detector to said reference point for said object.

* * * * *